US011298380B2

(12) United States Patent
Kooreman et al.

(10) Patent No.: US 11,298,380 B2
(45) Date of Patent: Apr. 12, 2022

(54) IPSC-BASED VACCINE AS A PROPHYLACTIC AND THERAPEUTIC TREATMENT FOR CANCER

(71) Applicants: Khloris Biosciences, Inc., Saratoga, CA (US); THE BOARD OF TRUSTEES OF THE LELAND STANFORD JUNIOR UNIVERSITY, Stanford, CA (US)

(72) Inventors: Nigel G. Kooreman, The Hague (NL); Joseph C. Wu, Palo Alto, CA (US); Lynne A. Bui, Saratoga, CA (US)

(73) Assignees: Khloris Biosciences, Inc., Saratoga, CA (US); THE BOARD OF TRUSTEES OF THE LELAND STANFORD JUNIOR UNIVERSITY, Stanford, CA (US)

( * ) Notice: Subject to any disclaimer, the term of this patent is extended or adjusted under 35 U.S.C. 154(b) by 279 days.

(21) Appl. No.: 16/237,705

(22) Filed: Jan. 1, 2019

(65) Prior Publication Data
US 2019/0290697 A1 Sep. 26, 2019

Related U.S. Application Data

(60) Provisional application No. 62/612,826, filed on Jan. 2, 2018.

(51) Int. Cl.
*A61K 35/12* (2015.01)
*A61K 35/28* (2015.01)
*A61K 35/35* (2015.01)
*A61K 35/545* (2015.01)
*A61K 35/33* (2015.01)
*A61K 39/39* (2006.01)
*A61P 35/00* (2006.01)
*A61K 39/00* (2006.01)

(52) U.S. Cl.
CPC .............. *A61K 35/28* (2013.01); *A61K 35/33* (2013.01); *A61K 39/0005* (2013.01); *A61K 39/39* (2013.01); *A61P 35/00* (2018.01); *A61K 2039/55516* (2013.01); *A61K 2039/55561* (2013.01); *A61K 2039/55572* (2013.01); *A61K 2039/55577* (2013.01); *A61K 2039/585* (2013.01)

(58) Field of Classification Search
None
See application file for complete search history.

(56) References Cited

U.S. PATENT DOCUMENTS

2015/0216957 A1 * 8/2015 Markosian ............ A61K 35/50
424/85.2
2016/0024469 A1  1/2016 Wu

FOREIGN PATENT DOCUMENTS

WO  WO200620889    2/2006
WO  WO2017087763   5/2017
WO  WO2017202949  11/2017

OTHER PUBLICATIONS

Li et al. Vaccination with Human Pluripotent Stem Cells Generates a Broad Spectrum of Immunological and Clinical Responses Against Colon Cancer. Stem Cells 2009;27:3103-3111.*
Diecke et al. Novel codon-optimized mini-intronic plasmid for efficient, inexpensive, and xeno-free induction of pluripotency. Scientific Reports, 2015, 5 : 8081.*
Kooreman et al. Autologous iPSC-Based Vaccines Elicit Anti-tumor Responses In Vivo. Cell Stem Cell 22, 501-513, Apr. 5, 2018.*
Yaddanapudi et al. (2012) Vaccination with Embryonic Stem Cells Protects against Lung Cancer: Is a Broad-Spectrum Prophylactic Vaccine against Cancer Possible? PLoS ONE 7(7): e42289.*
Zhao Tongbio et al.; "Immunogenecity of induced pluripotent stem cells" Nature, vol. 474, No. 7350, Jun. 9, 2011.
Diecke S. et al.; "Novel codon-optimized mini-intronic plasmid for efficient, inexpensive and xeno-free induction . . . " Scientific Reports, Vo. 5, No. 1, 8081, Jan. 28, 2015.
Li, Y., Zeng, et al. "Vaccination with human pluripotent stem cells generates a broad spectrum of . . . ". Stem Cells 27, 3103-3111, 2009.
Yi Li et al.; "Vaccination with Human Pluripotent Stem Cells Generates a Broad Spectrum of Immunological . . . ", Stem Cells, vol. 27, No. 12, Dec. 2012.
Wei Dong et al.; "Administration of Embryonic Stem Cells generates effective antitumor immunity . . . " Cancer Immunology, Immunotherapy, vol. 59, No. 8, Aug. 4, 2010.
Mocan T. & Iancu C.; Effective colon cancer prophylaxis in mice using embryonic stem cells and carbon nantubes: Internal. Journ. of Nanomedicine, vol. 6, Sep. 12, 2011.
Zhang Zu-Juan et al.; "Human Embryonic Stem Cells—a Potential Vaccine for Ovarian Cancer" Asian Pacific Journal of Cancer Prevention; vol. 13, No. 9, Sep. 30, 2012.
Yaddanapudi K. et al.; Vaccination with embryonic stem cells protects against lung cancer: is a broad spectrum . . . PLOS One, vol. 7, No. 7, E42289, Jul. 31, 2012.
Zhang Zujuan et al.; "Vaccination with embryonic stem cells generates effective antitumor imunity . . . " Inter. Journ. of Molecular Medicine, vol. 31, No. 1, Jan. 2013.
Zheng Qi et al.; "A hepatic stem cell vaccine is superior to an embryonic stem cell vaccine in the prophylaxis and treatment . . . " Oncology Reports, vol. 37, No. 3, Mar. 2017.
Kooreman N. G. et al.; "Autologous iPSC-Based Vaccines Elicit Anti-tumor Responses In Vivo"; Cell Stem Cell, vol. 22, No. 4, Apr. 5, 2018.

(Continued)

*Primary Examiner* — Nianxiang Zou
(74) *Attorney, Agent, or Firm* — Sam L. Nguyen; HDC IP Law, LLP

(57) ABSTRACT

In one embodiment, the application discloses a method for the treatment of cancer in a patient, the method comprises a vaccination of the patient with a vaccine, wherein the vaccine comprises an effective amount of mammalian pluripotent stem cells obtained from an embryonic source or obtained by reprogramming of somatic cells from the patient, wherein the vaccination comprising the step of administering a mammalian pluripotent stem cells to the patient in need thereof; and vaccine formulations for use in the treatment of cancer.

18 Claims, 8 Drawing Sheets

(56) References Cited

OTHER PUBLICATIONS

De Almeida P.E. et al.; "Transplanted terminally differentiated induced pluripotent stem cells are accepted by . . . " Nature Communications, vol. 5, No. 1, 3903, May 30, 2014.

Kooreman, N. G. & Wu J. C.; "Tumorigenicity of pluripotent stem cells: biological insights . . . " Journal of the Royal Society Interface, vol. 7, No. Suppl. 6, Dec. 6, 2010.

K. Okita et al., "Generation of germline-competent induced pluripotent stem cells", Nature, vol. 448, 313-318, Jul. 2007.

* cited by examiner

IPSC-BASED VACCINE AS A PROPHYLACTIC AND THERAPEUTIC TREATMENT FOR CANCER

CROSS-REFERENCE TO RELATED APPLICATION

This application claims the priority under 35 USC 119(e) of Provisional Application No. 62/612,826, filed Jan. 2, 2018, the disclosure of which is incorporated into this application by reference.

BACKGROUND OF THE INVENTION

Nearly a century ago, researchers observed that immunization with embryonic materials led to the rejection of transplanted tumors. More recently, shared transcriptome profiles and antigens were identified on various tumor cells and embryonic cells. This has led to the hypothesis that embryonic stem cells (ESCs) can be used as immunization agents to promote an anti-tumor response.

One key to the success of whole cell vaccination over traditional vaccines, which consist of inactivated organisms or protein products, is that a broad range of antigens can be presented to T-cells, including unknown antigens. However, the use of fetal and embryonic materials as vaccines to induce anti-tumor immunity has not yet advanced beyond animal models, owing largely to ethical challenges surrounding these therapies.

The discovery of induced pluripotent stem cells (iPSCs) allows pluripotent cells from a patient's own tissues to be created that share nearly identical gene expression and surface marker profiles with ESCs, circumventing a major ethical roadblock.

iPSCs are an attractive candidate for cancer vaccination because of the tumorigenic (Kooreman and Wu, 2010; Okita et al., 2007) and immunogenic (de Almeida et al., 2014; Zhao et al., 2011) properties of iPSCs with autologous transplantation that suggest potential efficacy in cancer vaccination. Importantly, autologous iPSCs may provide a more accurate and representative panel of a patient's tumor antigens than allogeneic ESCs.

SUMMARY OF THE INVENTION

In one embodiment, the present application provides compositions and methods for the generation of a cancer vaccine targeting multiple types of cancer, either prophylactically or therapeutically. In one aspect, the immunity against cancer cells generated by the vaccine combines an adjuvant and iPSCs or mini-intronic plasmid-generated iPSCs (MIP-iPSCs), such as the adjuvant CpG and iPSCs, or the adjuvant CpG and MIP-iPSCs. MIP-iPSCs are generated using a mini-intronic plasmid that activates a large repertoire of immune cells to target shared cancer-related or cancer-associated epitopes between iPSCs and cancer cells and provide long-term immunity against the development and/or progression of cancer.

In another aspect, the cancer types of interest are potentially unlimited, with initial pilot studies showing effectiveness in breast cancer, melanoma, pancreatic cancer and mesothelioma. Based on a large overlap in cancer epitopes between iPSCs and cancer cells, immunity may develop against solid tumors (e.g., breast, lung, skin, glioblastoma, head & neck, thyroid, pancreatic, hepatic, colorectal, kidney, gastric, sarcoma, ovarian, bladder, prostate, esophageal, endometrial, cervical) as well as hematological cancers (e.g., Hodgkin's lymphoma, non-Hodgkin's lymphoma, multiple myeloma, myeloproliferative disorders, leukemia).

In one embodiment, methods are provided for autologous cancer vaccine generation and vaccination regimen, the methods comprising of in-vitro generation of the iPSC-based vaccine and vaccinating, such as subcutaneously vaccinating the recipient for several weeks, including consecutive weeks, for example, 4 consecutive weeks. In one variation, the vaccination is performed weekly for at least 2 consecutive weeks, 3 consecutive weeks, 4 consecutive weeks, 5 consecutive weeks, or at least 6 consecutive weeks. In another variation, the vaccine comprises the use of iPSC together with the adjuvant CpG or any other adjuvant with comparable properties, wherein the adjuvant is an immunological agent, such as an antibody, peptide or small molecule, to boost or enhance the immune response towards the vaccine.

In one embodiment, where the pluripotent stem cells are not genetically engineered to overexpress pro-inflammatory proteins (e.g., by using GM-CSF, INFγ, DNMT inhibitor) or overexpress pro-immunogenic proteins (e.g., MHC class I, β2m, Tapasin, or c-Myc/Oct4). In one variation, the pluripotent stem cells are genetically engineered to overexpress pro-inflammatory proteins (e.g., by using GM-CSF, INFγ, DNMT inhibitor) or overexpress pro-immunogenic proteins (e.g., MHC class I, β2m, Tapasin, or c-Myc/Oct4). The methods for genetically overexpressing pro-immunogenic antigens to upregulate the immune response to the vaccine are described in Yaddanapudi, K. et al. (2012). Vaccination with embryonic stem cells protects against lung cancer: is a broad-spectrum prophylactic vaccine against cancer possible? PLoS ONE 7, e42289.

In another embodiment, where the pluripotent stem cells are genetically engineered to over-express one or more cancer antigens (e.g., CEA, MAGE-1, survivin, p53, HER2-neu, AFP, ras), pro-inflammatory proteins and/or pro-immunogenic proteins. In another embodiment, the vaccine can be generated from the patients' own tissue (e.g., skin, muscle, fat, bone marrow, organ, hair, blood and urine, or a combination of tissues) using iPSCs, thereby creating a patient-specific vaccine.

In one embodiment, there is provided a method for the treatment of cancer in a patient, the method comprises a vaccination of the patient with a vaccine, wherein the vaccine comprises an effective amount of mammalian pluripotent stem cells obtained from an embryonic source or obtained by reprogramming of somatic cells from the patient or another patient or human, or as obtained from allogeneic sources of iPSCs, wherein the vaccination comprises the step of administering mammalian pluripotent stem cells to the patient in need thereof. As used herein, the method is equally applicable to any mammal that can be referred to as a patient for the treatment of cancer.

In one variation of the method, the mammalian pluripotent stem cells are derived from a non-specified somatic cell. See Rajasingh, J. Prog. Mol. Biol. Transl. Sci., 2012, 111: 51-82 for a summary of the methods for the reprogramming of somatic cells and a method for regenerating patient-specific stem cells of any cell lineage without the use of embryonic stem cells. In one variation, the iPSCs are generated by genomic reprogramming using viral and non-integrating nonviral methods. In another variation, the pluripotent stem cells are formulated with an adjuvant, such as the pluripotent stem cells being combined with or emulsified in the adjuvant.

In one aspect of the above method, the pluripotent stem cells are induced pluripotent stem cells (iPSCs). In another aspect of the method, the mammalian pluripotent stem cells are undifferentiated pluripotent stem cells. In another aspect of the method, the pluripotent stem cells are generated using a mini-intronic plasmid containing four reprogramming factors comprising Oct4, c-Myc, KLF-4 and Sox2, with the possible addition of shRNA p53. In one variation of the method, the pluripotent stem cells are not genetically engineered to overexpress immunogenic proteins, such as by using GM-CSF. In another variation of the method, the pluripotent stem cells are genetically engineered to overexpress cancer antigens, pro-inflammatory proteins, and/or pro-immunogenic proteins. In one embodiment, where the pluripotent stem cells are genetically engineered to overexpress pro-inflammatory proteins (e.g., by using GM-CSF, INFg, DNMT inhibitor), or overexpress pro-immunogenic proteins (e.g., MHC class I, β2m, Tapasin, or c-Myc/Oct4), or over-express one or more cancer antigens (e.g., CEA, MAGE-1, survivin, p53, HER2-neu, AFP, ras), or overexpress pro-inflammatory proteins and/or pro-immunogenic proteins. In another embodiment, where the vaccine can be generated from the patients' own tissue (e.g., skin, muscle, fat, bone marrow, organ, hair, blood and urine, or a combination of tissues) using iPSCs, thereby creating a patient-specific vaccine. In another aspect of the method, the pluripotent stem cells comprise of partially differentiated embryoid bodies.

In another aspect of the above method, the stem cells are selected from the group consisting of fibroblast, keratinocytes, peripheral blood cells and renal epithelial cells. In one variation of the method, the pluripotent stem cells comprise cell fragments or epitopes associated with pluripotency. In another variation, the vaccine is irradiated prior to vaccination. In another variation, the vaccine is administered by subcutaneous injection and is administered for less than or equal to 4 weeks. In one variation of the method, the vaccination is performed weekly. In another variation, the vaccine may be administered daily, several times a week such as twice or three times a week, or every two weeks, and the duration could be two, three, four, five, six, seven, or 8 weeks.

In another aspect of the above method, the adjuvant is an immunological agent to boost the immune response towards the vaccine. A therapeutically effective dose of the vaccine can boost or enhance the in vivo immune response by at least about 10%, at least about 20%, at least about 30%, at least about 50%, at least about 75%, at least about 90% or more, relative to the effect in the absence of administering the vaccine of the present application. Assays used to measure T-cell response include, but not limited to, delayed-type hypersensitivity testing, flow cytometry using peptide major histocompatibility complex tetramers, lymphoproliferation assay, enzyme-linked immunosorbant assay (ELISA), enzyme-linked immunospot assay (ELISpot), cytokine flow cytometry, cytotoxic T-lymphocyte (CTL) assay, CTL precursor frequency assay, T-cell proliferation assays, carboxyfluorescein diacetate succinimidyl ester assays, polyfunctional T-cell assays, measurement of cytokine mRNA by quantitative reverse transcriptase polymerase chain reaction (RT-PCR), and limiting dilution analysis. Other assays to evaluate immune responses include, but not limited to, gene expression profiling, protein microarrays to evaluate antibody responses to multiple antigens at one time, luciferase immunoprecipitation, phosphoflow for measuring multiple intracellular signaling molecules in the immune system at a single-cell level for lymphocyte immune monitoring, and surface plasmon resonance biosensors to monitor antibody immunity in serum. In one variation of the method, the adjuvant is selected from the group consisting of CpG, QS21, poly(di(carboxylatophenoxy)phosphazene; derivatives of lipopolysaccharides such as monophosphoryl lipid A, muramyl dipeptide (MDP; Ribi), threonyl-muramyl dipeptide (t-MDP; Ribi); OM-174; cholera toxin (CT), and Leishmania elongation factor; or mixtures thereof.

In another aspect of the method, the vaccine is administered as an adjuvant therapy after tumor resection. In one variation of the method, the vaccine is administered in conjunction with chemotherapy, other immunotherapy such as antibodies, and small molecules, including nanoparticles containing these agents or molecules. In another variation, the vaccine can be given in the neo-adjuvant (before surgery), adjuvant (after surgery), or metastatic setting or before cancer develops in the preventative setting. In another aspect of the method, the vaccine is administered as a neoadjuvant therapy before tumor resection. In another aspect of the method, the vaccine is administered as therapy in the metastatic setting. In another aspect of the method, the vaccine is administered in combination with single or multiple chemotherapeutic agents, immunotherapies, e.g. anti-PDL1, anti-PD1, or anti-CTLA4 antibodies, other biologics, and small molecules, e.g., diprovocim, including nanoparticles containing these agents. In another aspect of the method, the cancer is selected from the group consisting of breast cancer, melanoma and mesothelioma. In yet another aspect of the method, the cancer is selected from the group consisting of leukemia, multiple myeloma, lymphoma, myeloproliferative disorders, squamous cell cancer, adenocarcinoma, sarcoma, neuroendocrine carcinoma, bladder cancer, skin cancer, brain and spinal cord cancers, head and neck cancer, bone cancer, breast cancer, cervical cancer, colon cancer, rectal cancer, endometrial cancer, gastrointestinal cancers, (hypo) laryngeal cancer, esophageal cancer, germ cell cancer, transitional cell cancer, liver cancer, lung cancer, pancreatic cancer, cholangiocarcinoma, poorly differentiated carcinoma, prostate cancer, eye cancer, renal cell cancer, ovarian cancer, gastric cancer, testicular cancer, thyroid and thymus cancer.

In another embodiment, there is provided a method for the vaccination of a mammal with a pluripotent stem cell cancer vaccine, the method comprising: introducing the mammalian pluripotent stem cells from 1) an embryonic source, or 2) by reprogramming from a somatic cell from the recipient; and providing the recipient with pluripotent stem cells. In another aspect of the method, the mammalian cells are undifferentiated pluripotent cells.

In one aspect of the method, the pluripotent stem cells are generated using a mini-intronic plasmid containing four reprogramming factors comprising Oct4, c-Myc, KLF-4 and Sox2. In one variation of the method, the pluripotent stem cells are not genetically engineered to over-express immunogenic proteins, such as by using GM-CSF. In one variation of the method, the pluripotent stem cells are genetically engineered or altered to over-express immunogenic proteins, such as by using GM-CSF.

In another aspect of the method, the pluripotent stem cells are genetically engineered to over-express cancer antigens and/or immunogenic proteins. In another aspect of the method, the pluripotent stem cells are selected from the group consisting of fibroblast, keratinocytes, peripheral blood cells and renal epithelial cells. In one variation of the method, the pluripotent stem cells comprise cell fragments or epitopes associated with pluripotency.

In another aspect of the above method, the vaccine is irradiated prior to vaccination. In one variation of the method, the vaccine is subcutaneously injected for the duration of less than or equal to 4 weeks, such as 3 weeks, 2 weeks or about 1 week. In another variation, the vaccination is performed weekly. In another variation, the vaccination may be performed daily, several times a week such as twice or three times a week, or every two weeks, and the duration may be two, three, four, five, six, seven, or 8 weeks, or more.

In another aspect of the above method, the vaccine further comprises an adjuvant that is an immunological agent to boost the immune response towards the vaccine. In one variation of the above methods, the adjuvant vaccination after tumor resection results in clean resection areas (RAs) and a reactivation of the immune system to target the cancer cells. In another variation of each of the above methods, the method provides at least one of a tumor specific response, an effective antigen presentation, a positive T-helper immune response and results in cytotoxic T-cell activities.

In one variation of the method, the method of treatment results in no sign of autoimmune responses due to vaccine; or the method of treatment results in substantially no detectable sign of autoimmune responses due to vaccine. In another variation of the method, the vaccine is employed as an adjuvant therapy after tumor resection. In one variation, the method provides the patient with at least one adjuvant round; or at least two adjuvant rounds of (C+I) vaccine with no visible recurrence of the cancer, such as melanoma or breast cancer, or the cancers as recited herein. In another variation, the method results in an upregulation of mature antigen presenting cells (APCs) and an upregulation of helper T-cells.

In another variation, the vaccine reactivates the immune system in rejecting remnant cancer cells, such as melanoma cells, by at least one of the systemic upregulation of IL-4 expressing B-cells, TNF-alpha expressing $CD11b^+GR1hi$ myeloid cells and a reduction of tumor-promoting Th17 cells. In another variation, the method results in inducing tumor degradation, including degradation near the tumor injection site and the vaccination site. In one variation, the method results in the reduction of the tumor size, by at least 10%, 20%, 30%, 40%, 50%, 75%, 85%, 90% or more than 95% after treatment. In another variation, the method results in the priming of the immune system and the reactivation of the immune system and specifically targets the cancer cells. In another variation of each of the above method, the method may be employed as adjuvant immunotherapy for multiple cancer types, and may be effective within 1 week, 2 weeks, 3 weeks, 4 weeks or within about 5 weeks after diagnosis. In another variation, the method provides a prophylactic immunization that results in an effective and specific response to multiple cancer types. In another variation, the effective and specific response results from an upregulation of mature APCs in the lymph nodes with a subsequent increase in helper T-cells and cytotoxic T-cells locally; and after a period of time, also an increase in helper T-cells and cytotoxic T-cells systematically. In another variation, B-cells and T-cells expressing IL-2, IL-4, and IL-5 may be predictive for tumor regression in the vaccination.

In another variation of the method, the vaccination creates broad tumor immunity against multiple cancer types and presents the immune system with large quantities (may include several dozens and up to hundreds or thousands) of tumor antigens. In another variation of the method, the vaccination reactivates the immune system in targeting established cancers without therapy-associated adverse effects (e.g., autoimmune response, weight loss, cytokine release syndrome and combination thereof) and the method can be created within a few weeks after diagnosis. Accordingly, the method presents a viable option for personalized adjuvant immunotherapy shortly after conventional primary treatment of cancer. In another variation of the method, the vaccines are administered by intramuscular, intradermal, subcutaneous, intravenous, intraarterial, intrasplenic, intranodal, intratumoral or by intranasal methods.

In another embodiment, there is provided a thermally stable vaccine composition comprising an effective amount of mammalian pluripotent stem cells obtained from an embryonic source or obtained by reprogramming of somatic cells from a mammalian, and optionally, an adjuvant or an immunological agent to boost the immune response towards the vaccine. In one variation, the thermally stable vaccine or heat stable vaccine allows for storage that does not require cold chain storage, allowing the facile introduction of the vaccines in areas with no or limited cold chain storage capacity. In one variation, the vaccine further comprises an effective amount (such as an approximate range of 0.01% to 1% wt/wt, 0.05% to 0.5% wt/wt, 0.05% to 1% wt/wt, or 0.01% to 0.5% wt/wt) of a glycol, such as propylene glycol, polyethylene glycol 300 and glycerin, or mixtures thereof. In another variation, the vaccine is stable for up to 6 months, up to 12 months, up to 24 months or up to 36 months at about 35° C., either as a standard liquid formulation or as a spray dried formulation.

One aspect of the drying method for the vaccine includes a spray drying method. The spray-drying method may include, for example, a method for spraying from a high-pressure nozzle, or by using a centrifugal force, such as an atomizer as known in the art. The gas or air that may be used for the spray drying includes heated air or hot air at a temperature sufficient to dry the vaccine powder having the desired moisture content. In one aspect, the gas is an inert gas such as nitrogen or nitrogen-enriched air.

In one aspect, the hot gas temperature may be at about 30° C. to 50° C., 30° C. to 60° C., 30° C. to 70° C., or about 30° C. to 100° C. The high pressure that may be used for the spray during process used in a high pressure nozzle may include about 10 to 1,000 psi, 100 to 800 psi or 200 to 500 psi. The spray drying may be carried out under conditions such that the residual water or residual moisture content of the dry vaccine may be controlled to about 1% to about 6%, 1% to 5%, 2% to 6%, 3% to 6% or about 3% to 5%.

In one aspect, the emulsions may then be sprayed dried in conventional spray drying equipment from commercial suppliers, such as Buchi, Niro, Yamato Chemical Co., Okawara Kakoki Co., and similar commercially available spray drier. Spray drying processes, such as rotary atomization, pressure atomization and two-fluid atomization may also be used. Examples of the devices used in these processes include Parubisu Mini-Spray GA-32 and Parubisu Spray Drier DL-41 (Yamato Chemical Co.) or Spray Drier CL-8, Spray Drier L-8, Spray Drier FL-12, Spray Drier FL-16 or Spray Drier FL-20, (Okawara Kakoki Co.), may be used for the spray drying method using rotary-disk atomizer. The nozzle of the atomizer that produces the powder of the present application may include, for example, nozzle types 1A, 1, 2A, 2, 3 (Yamato Chemical Co.) or similar commercially available nozzles, may be used for the above-mentioned spray drier. In addition, disks type MC-50, MC-65 or MC-85 (Okawara Kakoki Co.) may be used as rotary disks of the spray-drier atomizer.

In another aspect, the vaccine powder obtained from the drying process may comprise 1% by weight, 5% by weight, 7% by weight, 10% by weight, 20% by weight, 30% by weight, 40% by weight, 50% by weight or more of particles having an average particle size in the range from about 5 to 1,000 microns, from about 10 to 500 microns, from 10 to 350 microns, from 20 to 250 microns, from 40 to 200 microns, or about 50 to 150 microns. In one aspect, the powder obtained from the drying process comprises of about 1% to 10% by weight of particles with an average particle size of 50 to 150 microns.

In another aspect of the vaccine composition, the pluripotent stem cells are induced pluripotent stem cells (iPSCs). In another aspect of the vaccine composition, the mammalian pluripotent stem cells are undifferentiated pluripotent stem cells. In another aspect of the vaccine composition, the stem cells are selected from the group consisting of fibroblast, keratinocytes, peripheral blood cells and renal epithelial cells.

In yet another aspect of the vaccine composition, the adjuvant is selected from the group consisting of CpG, QS21, poly(di(carboxylatophenoxy)phosphazene; derivatives of lipopolysaccharides such as monophosphoryl lipid A, muramyl dipeptide (MDP; Ribi), threonyl-muramyl dipeptide (t-MDP; Ribi); OM-174; cholera toxin (CT), and Leishmania elongation factor.

In one variation, the application discloses a formulation for use in the treatment of cancer in a patient, comprising a vaccination of the patient with a vaccine, wherein the vaccine comprises an effective amount of mammalian pluripotent stem cells obtained from an embryonic source or obtained by reprogramming of somatic cells from the patient, wherein the vaccination comprising the step of administering a mammalian pluripotent stem cells to the patient in need thereof.

In one variation of each of the methods as recited herein, there is provided a vaccination for use in treating cancer in a patient wherein the vaccine comprises an effective amount of mammalian pluripotent stem cells obtained from an embryonic source or obtained by reprogramming of somatic cells from the patient, wherein the vaccination comprising the step of administering mammalian pluripotent stem cells to the patient in need thereof. In another variation, the vaccine is a thermally stable vaccine composition comprising an effective amount of mammalian pluripotent stem cells obtained from an embryonic source or obtained by reprogramming of somatic cells from a mammalian, and an adjuvant or an immunological agent to boost the immune response towards the vaccine.

DETAILED DESCRIPTION OF THE INVENTION

Figure 1:
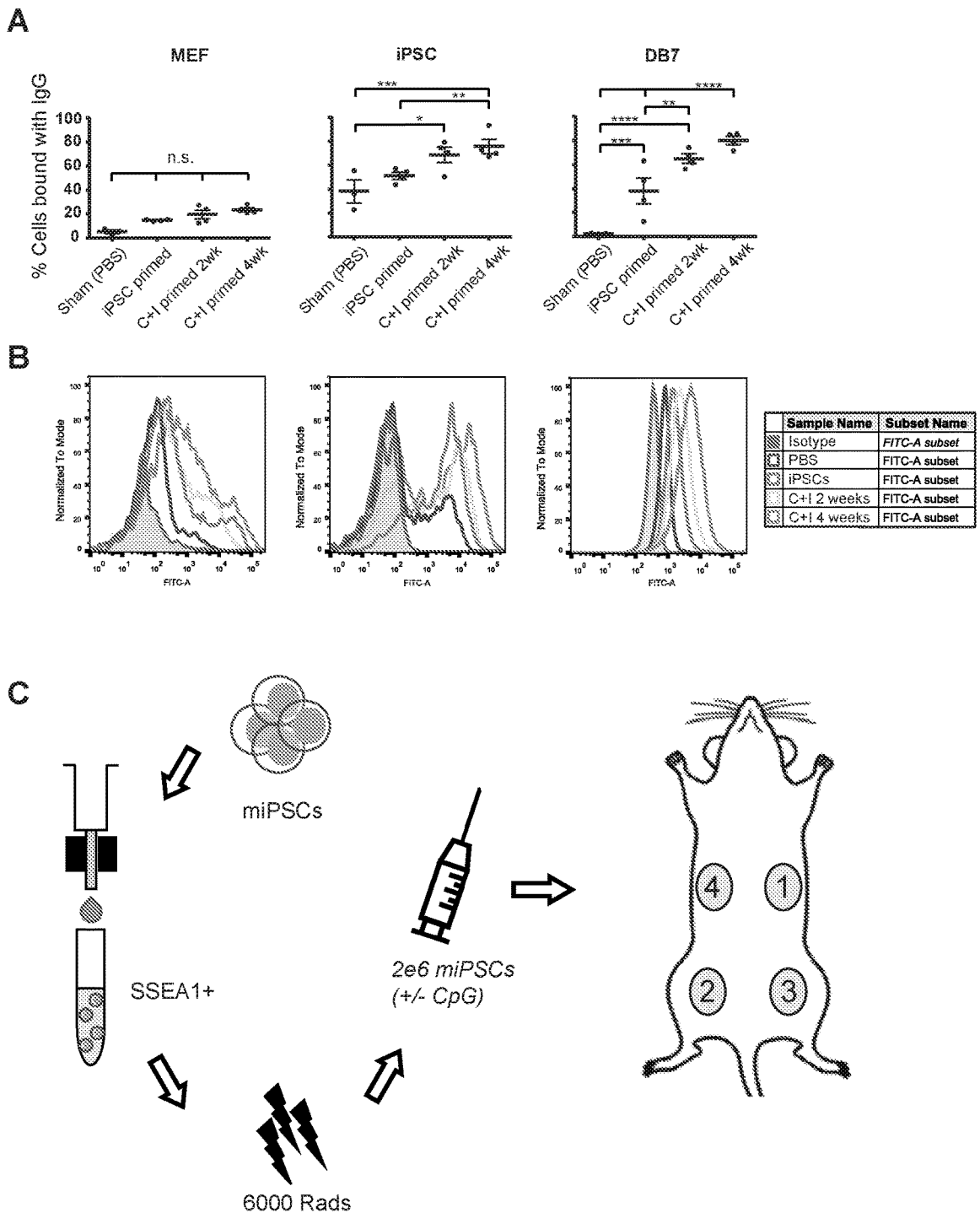
FIG. 1 is a representation showing the assessment of the optimal vaccination schedule by measuring maximal B-cell responses.

FIG. 1. Assessing the optimal vaccination schedule by measuring maximal B-cell responses. (a) Optimal vaccination was set to C+I vaccination weekly for four weeks, as assessed by % IgG binding to DB7, without a significant increase in non-specific MEF binding (n=3 control animals, n=4 iPSC primed animals, n=4 C+I primed 2 week, and n=4 C+I primed 4 week animals, mean±s.e.m., ANOVA with Tukey's multiple comparison test). (b) Representative FACS plot of serum IgG binding of PBS 4-week, iPSC 4-week, C+I 2-week, or C+I 4-week vaccinated mice to embryonic fibroblasts, iPSCs and DB7 cancer cells. As a control sample for differentiated cells, a partly differentiated cell culture was included in the analysis. This is shown by IgG positive and negative cells, indicating that the IgG binding is specific to the undifferentiated portion of the analyzed cells. C+I 4-week vaccinated mice showed the best IgG binding to DB7 breast cancer cells. (c) Schema showing vaccine preparation consists of sorting murine iPSCs for pluripotency, irradiation, resuspension in adjuvant solution, and subcutaneous injection in the flank, sites 1 to 4.

Figure 2:
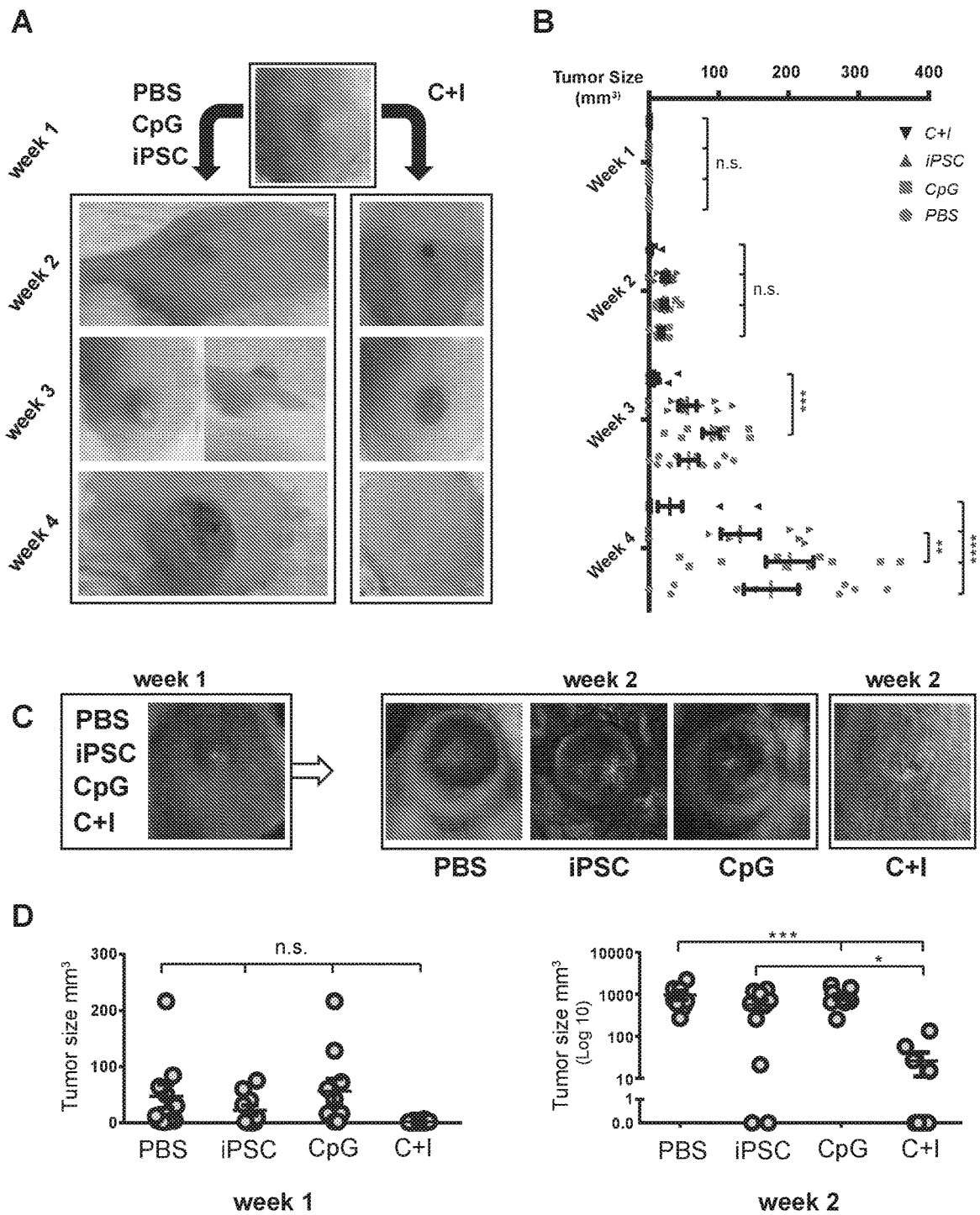
FIG. 2 is a representation showing the in vivo effectiveness of prophylactic treatment of breast cancer and melanoma in mice.

FIG. 2. In vivo effectiveness of prophylactic treatment of breast cancer and melanoma in mice. (a) Vaccination of FVB mice with the C+I vaccine resulted in a complete rejection of the cancer cells in 7 out of 10 mice by four weeks and overall reductions in DB7 tumor size (n=10 per group). (b,c) Quantification of the data presented in A. Vaccination of C57BL/6 mice with the C+I vaccine resulted in significant reduction of melanoma sizes initiated by the aggressive B16F0 melanoma cell line by week two (n=8PBS, n=9 iPSC primed, n=10 CpG primed, and n=9 C+I primed). (d) Quantification of the tumor size data presented in panel C. Data in b and d expressed as mean±s.e.m., ANOVA with Tukey's multiple comparison test, *$p<0.05$, $p<0.001$, *$p<0.001$, ****$p<0.0001$).

Figure 3:
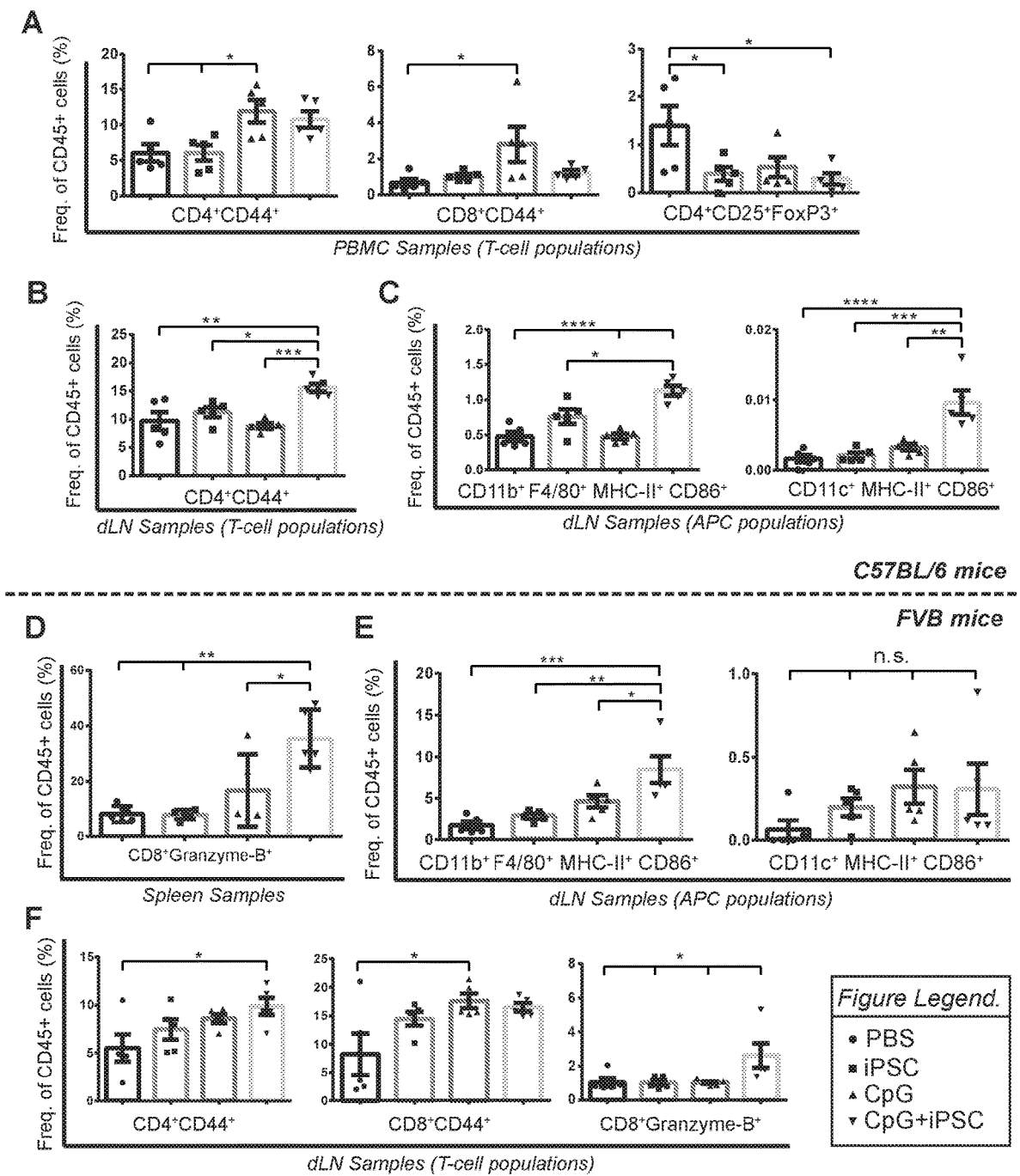
FIG. 3 is a representation showing that prophylactic vaccination leads to increased antigen presentation in dLNs and subsequent effector/memory T-cell responses in dLNs and spleen.

FIG. 3. Prophylactic vaccination leads to increased antigen presentation in dLNs and subsequent effector/memory T-cell responses in dLNs and spleen. (a) Two weeks after B16F0 introduction, iPSC and C+I vaccinated mice showed a significant reduction in percentages of regulatory T-cells (CD4$^+$CD25$^+$FoxP3$^+$) and an increase in effector/memory helper T-cells (CD4$^+$CD44$^+$) in the peripheral blood of C+I vaccinated mice. At that point, only limited upregulation of effector/memory cytotoxic T-cells (CD8+CD44$^+$) was seen. (b) The dLNs in the C+I group had significantly higher percentages of effector/memory helper T-cells and (c) increased antigen presentation by mature antigen presenting cells (APCs) such as macrophages (CD11b$^+$F4/80$^+$MHC-II$^+$CD86$^+$) and dendritic cells (CD11c$^+$MHC-II$^+$CD86$^+$). (d) C+I vaccinated FVB mice showed increased percentages of activated cytotoxic T-cells (CD8$^+$Granzyme-B$^+$) in spleens four weeks after DB7 introduction. (e) dLNs of these mice revealed an increased frequency of mature antigen-presenting macrophages as well as (f) effector/memory helper T-cells and cytotoxic T-cells. (n=5 per group, mean±s.e.m., ANOVA with Tukey's multiple comparison test, *p<0.05, p<0.001, *p<0.001, ****p<0.0001).

Figure 4:
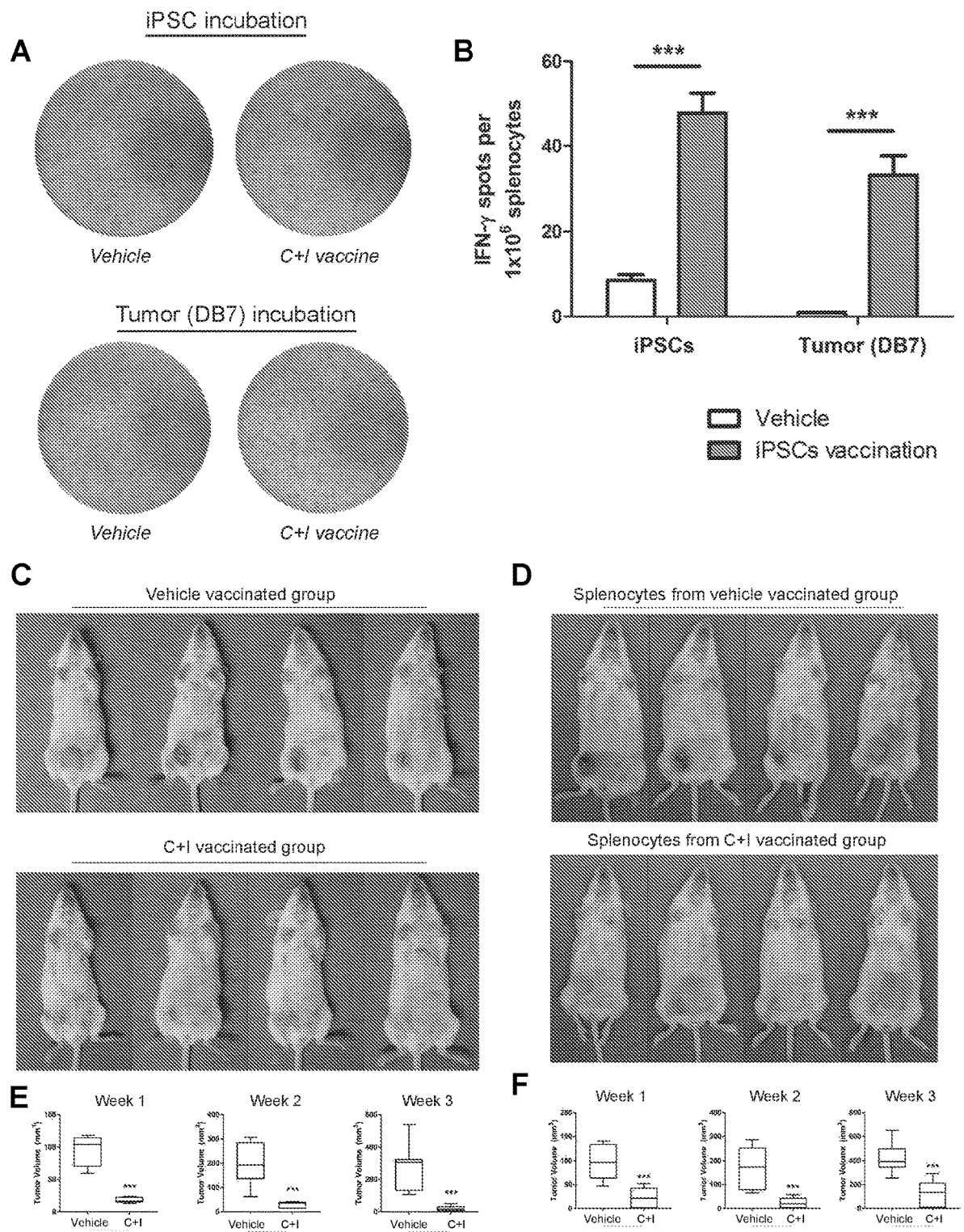
FIG. 4 is a representation showing tumor specific properties of C+I vaccine in vitro as well as in vivo in an orthotopic tumor model of breast cancer.

FIG. 4. Tumor specific properties of C+I vaccine in vitro as well as in vivo in an orthotopic tumor model of breast cancer. (a) Dual ELISPOT assay (red: granzyme-β, blue: IFN-γ) for immune cell activation of splenocytes in the C+I vaccinated group (iPSC vaccinated; n=6) compared to CpG alone (vehicle; n=4) group upon exposure to iPSC lysate and DB7 lysate (also see Figure S4A, B). (b) Significant increase of number of IFN-γ spots in C+I vaccinated group compared to the vehicle group. (Spots calculated by Adobe Photoshop software based on color differences. *p<0.001, Student's t-test). (c) Representative images of tumor volume in C+I vaccinated mice compared to vehicle mice in an orthotopic tumor model of breast cancer at three weeks after tumor inoculation. (d) Representative images of tumor volume in tumor bearing mice after receiving adoptive transfer of splenocytes from C+I vaccinated mice compared to vehicle mice in an orthotopic tumor model of breast cancer at three weeks after adoptive transfer. (e) Quantification of the results from panel C shows a significant reduction of tumor volume in C+I vaccinated mice compared to vehicle mice in an orthotopic tumor model of breast cancer over the course of three weeks. (f) Significant reduction of tumor volume in tumor-bearing mice from panel D over the course of three weeks after adoptive transfer of splenocytes from C+I vaccinated mice (n=7) compared to mice receiving splenocytes from vehicle vaccinated mice (n=8). (*p<0.001, one way ANOVA).

Figure 5:
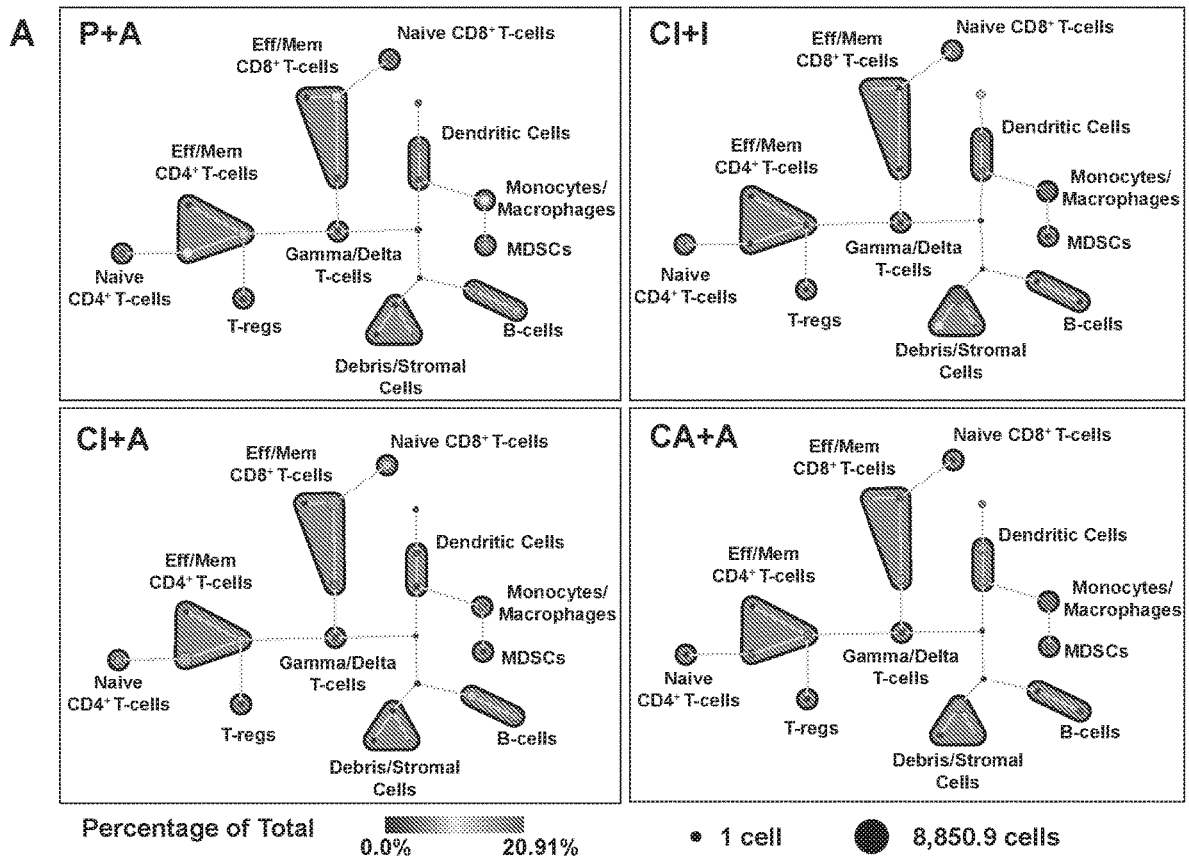
FIG. 5 is a representation showing that TILs show proinflammatory phenotype with B-cell and CD4$^+$ T-cell antitumor responses.
Figure 5:
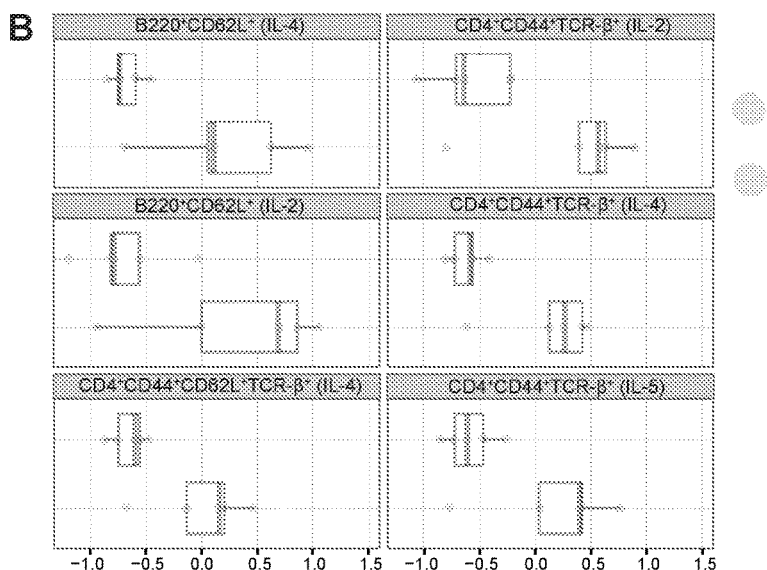

FIG. 5. TILs show a pro-inflammatory phenotype with B-cell and $CD4^+$ T-cell anti-tumor responses. (a) One week after $2 \times 10^6$ AC29 (A) mesothelioma cells were injected in CpG+iPSC (C+I) vaccinated mice (n=5), TILs in this C+I/A group showed an increase in the frequency of effector/memory $CD4^+$ and $CD8^+$ cells and a reduction in T-reg numbers, compared to PBS (P) vaccinated mice (n=5; P/A group), as assessed by SPADE analysis of CyTOF data. The positive control groups, C+I vaccinated and CpG+AC29 (C+A) vaccinated mice, fully rejected iPSCs (n=5; C+I/I) and AC29 cells (n=5; C+A/A), respectively, with a subsequently enhanced presence of monocytes and macrophages and stromal cells. (b) Citrus analysis of CyTOF data revealed that higher levels of IL-2, IL-4, and IL-5 in B-cell and helper T-cell clusters in the C+I mice are responsible for the intra-tumoral immune response.

Figure 6:
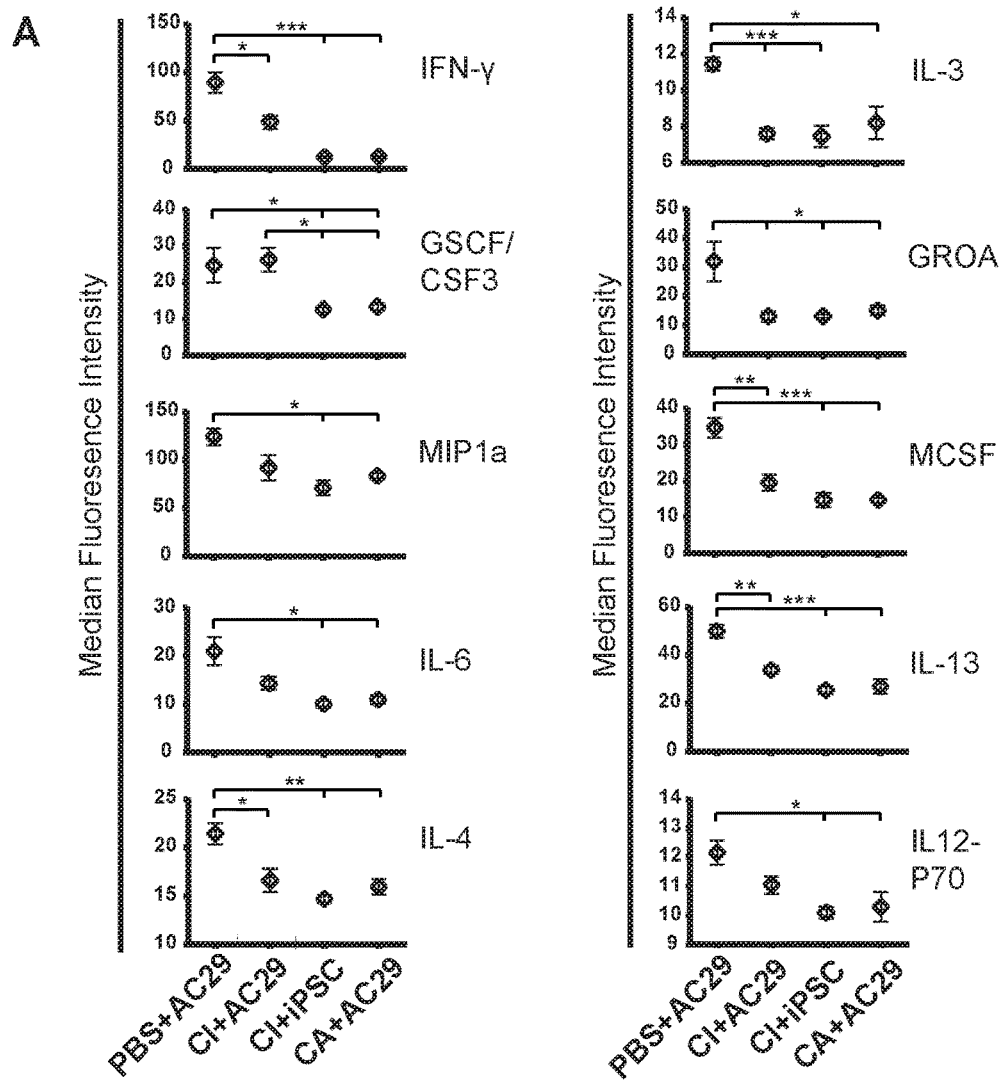
FIG. 6 is a representation showing C+I vaccination leads to a systemic immune profile similar to positive control groups of tumor rejection and upregulation of vaccine-specific T-cell clones.
Figure 6:
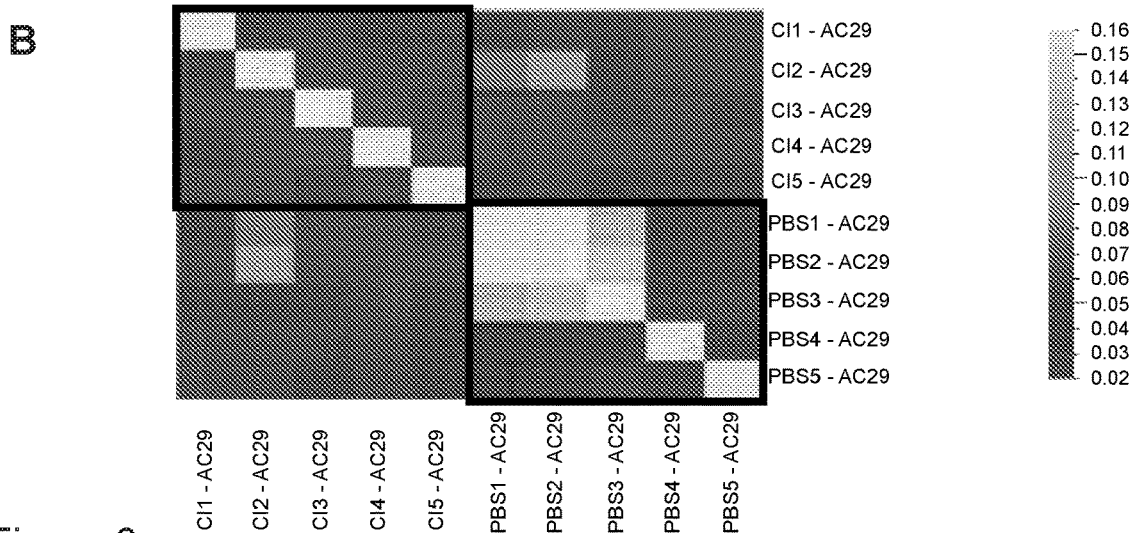

FIG. 6. C+I vaccination leads to a systemic immune profile similar to positive control groups of tumor rejection and upregulation of vaccine-specific T-cell clones. (a) Luminex analysis of serum from the different treatment groups at one week after tumor cell introduction reveals a significantly lower presence of systemic cytokines in the positive control mice (C+I/iPSC, C+A/AC29) compared to PBS control mice (PBS/AC29). The C+I/AC29 group follows a similar trend as the positive control samples (C+I/iPSC and C+A/AC29, ANOVA with Tukey's multiple comparison test, *p<0.05, p<0.001, *p<0.001). (b) Among C+I vaccinated mice (C+I1 through C+I5/AC29), there was greater unique vaccine-associated variance within the TILs, whereas PBS-vaccinated mice (PBS1 through 5/AC29) demonstrated a higher uniformity among T-cells that are commonly present in lymphoid organs (Figure S6C-D).

Figure 7:
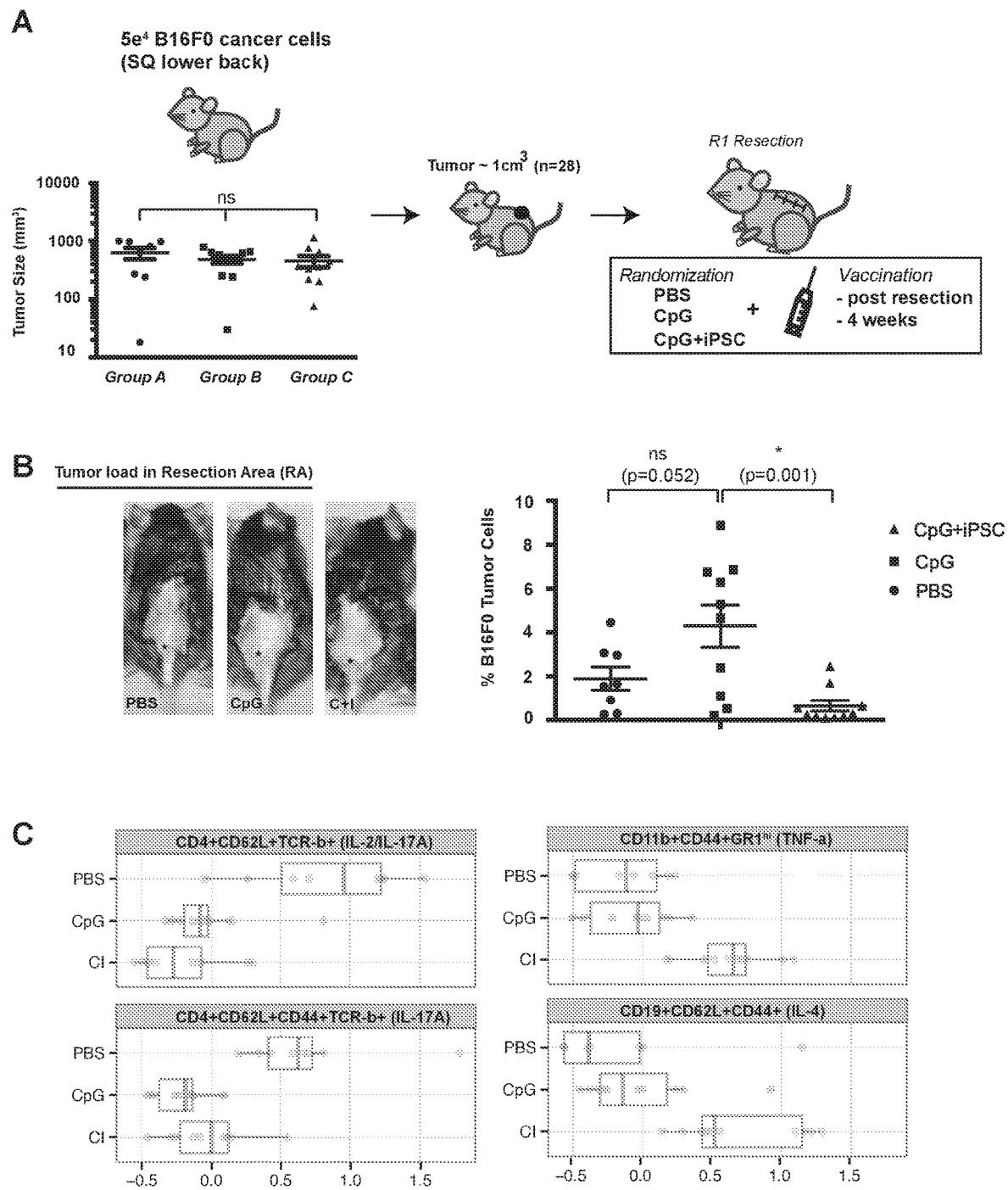
FIG. 7 is a representation showing that adjuvant vaccination after tumor resection leads to clean RAs and reactivation of the immune system to target cancer cells.
Figure 8:
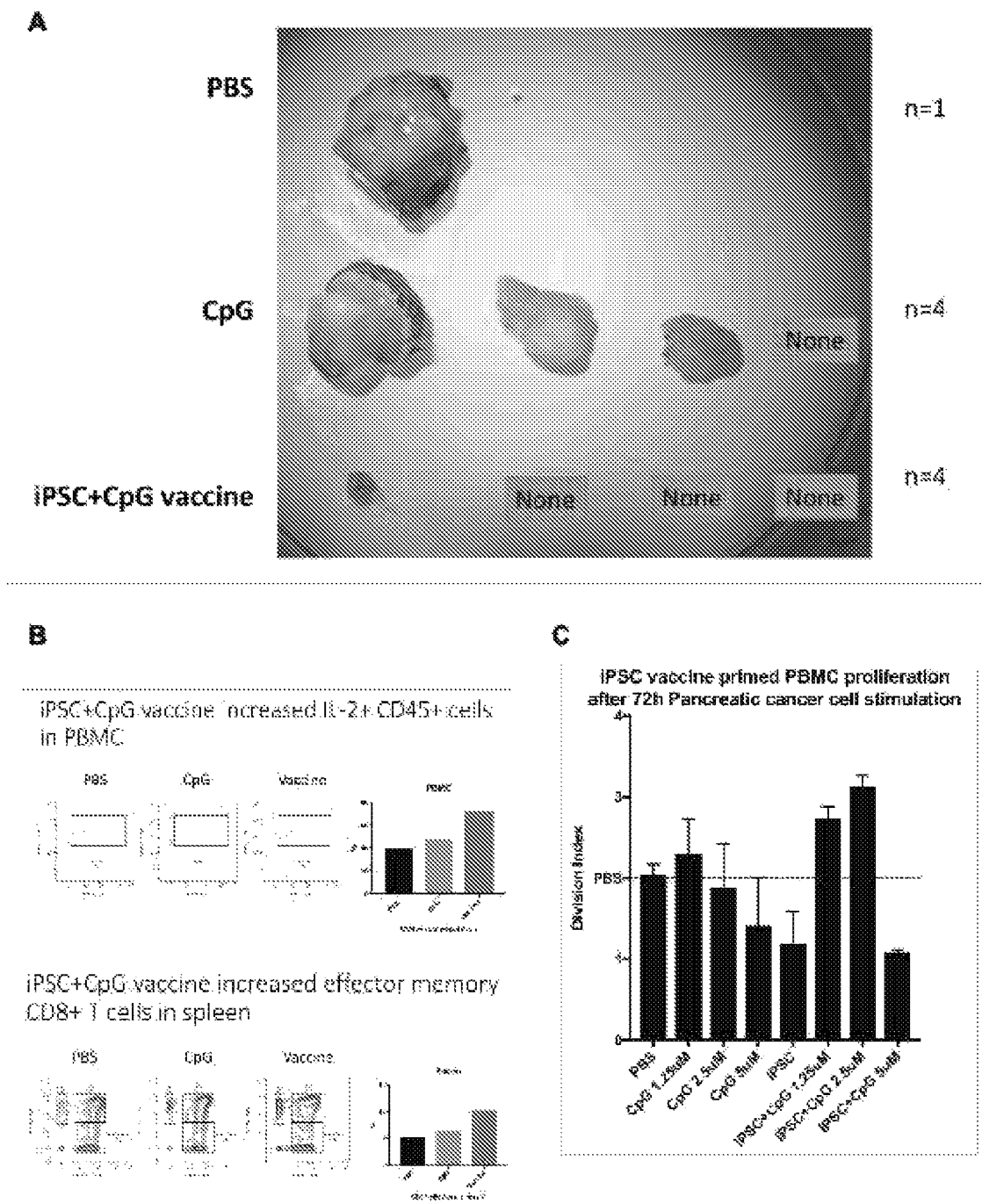
FIG. 8 include a graphical and descriptive representations showing A) the relative effects of tissues as PBS, CpG and iPSC plus CpG vaccine; B) iPSC+CpG vaccine increased IL-2+CD45+ cells in PBMC, and iPSC+CpG vaccine with increased effector memory CD8+ T cells in spleen; C) results of iPSC vaccine primed PBMC proliferation after 72 hrs of pancreatic cancer cell stimulation.

FIG. 7. Adjuvant vaccination after tumor resection leads to clean RAs and reactivation of the immune system to target cancer cells. (a) B16F0 tumor-bearing mice underwent R1 tumor resection, were randomized into different treatment groups, and were vaccinated weekly with either C+I, CpG, or PBS for four weeks. (b) DNA from skin biopsies (*) in resection areas (RAs) showed a significant reduction in the percentage of tumor cells after four vaccination rounds with the C+I vaccine, as assessed by ddPCR. (c) Vaccination post-tumor resection led to a reduction of Th17 cells ($CD4^+CD62L^+TCR-b^+(IL-2/IL-17A)$; $CD4^+CD62L^+CD44^+TCR-b^+(IL-17A)$) and an increased presence of TNF-α expressing myeloid cells ($CD11b^+CD44^+GR1^{hi}(TNF-α)$) and IL-4 expressing $CD19^+CD62L^+CD44^+$ B-cells (n=8PBS, n=10 CpG, n=10 C+I, mean±s.e.m., ANOVA with Tukey's multiple comparison test, *p<0.05). SQ: subcutaneous injection.

Compositions and methods are provided for the generation of the pluripotency vector (MIP), generation of iPSCs with this vector, establishing the cancer vaccine and vaccinating subjects prophylactically and therapeutically.

The cancer vaccine, as used herein, is the use of the host's pluripotent stem cells in combination with the adjuvant to prime the same host's immune system in targeting cancer cells.

The hosts are generally mammals, including but not limited to humans, dogs, cats, or horses. Laboratory animals, such as rodents are of interest for the cancer selections studies, epitope screening and mechanistic studies. Larger animal studies, e.g. pig and monkey are of interest for safety studies.

For the purpose of invention, pluripotent cells may be autologous, allogeneic or xenogeneic with respect to the recipient.

"Treatment" refers to both therapeutic treatment and prophylactic or preventative measures. Those in need of treatment include those already with the disorder as well as those in which the disorder is to be prevented. In another embodiment, "treating" or "treatment" of any condition or disorder refers, in certain embodiments, to ameliorating a condition or disorder that exists in a subject, including prophylactically. In another embodiment, "treating" or "treatment" includes ameliorating at least one physical parameter, which may be indiscernible by the subject. In yet another embodiment, "treating" or "treatment" includes modulating the condition or disorder, either physically (e.g., stabilization of a discernible symptom) or physiologically (e.g., stabilization of a physical parameter) or both. In yet another embodiment, "treating" or "treatment" includes delaying the onset of the condition or disorder. In yet another embodiment, "treating" or "treatment" includes the reduction or elimination of either the condition (e.g., pain) or one or more symptoms (e.g., pain) of the condition (e.g., cancer), or to retard the progression of the condition or of one or more symptoms of the condition, or to reduce the severity of the condition or of one or more symptoms of the condition. In yet another embodiment, "treating" or "treatment" includes administering a vaccine described herein prophylactically.

"Mammal" for purposes of treatment refers to any animal classified as a mammal, including humans, domestic and farm animals, and zoo, sports, or pet animals, such as dogs, horses, cats, cows, etc. In one aspect, the mammal is human.

By "pluripotency" and pluripotent stem cells, it is meant that such cells have the ability to differentiate into all types of cells in an adult organism. The term "induced pluripotent stem cell" encompasses pluripotent cells, that, like embryonic stem cells (ESCs), can be cultured over a long period of time while maintaining the ability to differentiate into all types of cells in an organism, but that, unlike ESCs (which are derived from the inner cell mass of blastocysts), are derived from differentiated somatic cells, that is, cells that had a narrower, more defined potential and that in the absence of experimental manipulation could not give rise to all types of cells in the organism. By "having the potential to become iPSCs" it is meant that the differentiated somatic cells can be induced to become, i.e. can be reprogrammed to become, iPSCs. In other words, the somatic cell can be induced to redifferentiate so as to establish cells having the morphological characteristics, growth ability and pluripotency of pluripotent cells. iPSCs have an human ESC-like morphology, growing as flat colonies with large nucleocytoplasmic ratios, defined borders and prominent nucleoli. In addition, iPSCs express one or more key pluripotency markers known by one of ordinary skill in the art, including but not limited to Alkaline Phosphatase, SSEA3, SSEA4, Sox2, Oct3/4, Nanog, TRA160, TRA181, TDGF 1, Dnmt3b, FoxD3, GDF3, Cyp26a1, TERT and zfp42. In addition, pluripotent cells are capable of forming teratomas. In addition, they are capable of forming or contributing to ectoderm, mesoderm, or endoderm tissues in a living organism.

Somatic cells, with a combination of three, four, five, six, or more factors can be de-differentiated/reprogrammed to a state apparently indistinguishable from embryonic stem cells (ESCs); these reprogrammed cells are termed "induced pluripotent stem cells" (iPSCs, iPCs, iPSCs) and can be produced from a variety of tissues.

The vaccines may also comprise an adjuvant. Adjuvants useful in vaccine are well known to those of skill in the art, and accordingly, the selection of an appropriate adjuvant can be performed routinely by one of skill in the art upon review of the present application. Examples of useful adjuvant include, but are not limited to, complete and incomplete Freund's, mineral gels such as aluminum hydroxide, surface active substances such as lysolecithin, pluronic polyols, polyanions, peptides and oil emulsions. In some embodiments, the vaccine is an injectable composition that is sterile, pyrogen free, formulated to be isotonic and free of particulates. The standards of purity required for injectable compositions are well known as are the production and purification methods used to prepare injectable compositions. The vaccines may be administered by any means known in the art. Pharmaceutical injectable compositions may be administered parenterally, i.e., intravenous, subcutaneous and intramuscular. In some embodiments, pharmaceutical vaccine compositions may be administered intranasally or to tissue in the oral cavity such as by administration sublingually or to buccal tissue.

The term "stem cell" refers to an unspecialized cell that is capable of replicating or self-renewing itself and developing into specialized cells of a variety of cell types. The product of a stem cell undergoing division is at least one additional cell that has the same capabilities as the original cell. The term "stem cell" is intended to encompass embryonal and adult stem cells, totipotent and pluripotent cells, and autologous cells, as well as heterologous cells. Stem cells and cultures thereof: Pluripotent stem cells are cells derived from any kind of tissue (usually embryonic tissue such as fetal or pre-fetal tissue), which stem cells have the characteristic of being capable under appropriate conditions of producing progeny of different cell types that are derivatives of all of the 3 germinal layers (endoderm, mesoderm, and ectoderm). These cell types may be provided in the form of an established cell line, or they may be obtained directly from primary embryonic tissue and used immediately for differentiation. Included are cells listed in the NIH Human Embryonic Stem Cell Registry, e.g. hESBGN-01, hESBGN-02, hESBGN-03, hESBGN-04 (BresaGen, Inc.); HES-1, HES-2, HES-3, HES-4, HES-5, HES-6 (ES Cell International); Miz-hES1 (MizMedi Hospital-Seoul National University); HSF-1, HSF-6 (University of California at San Francisco); and H1, H7, H9, H13, H14 (Wisconsin Alumni Research Foundation (WiCell Research Institute)). Induced pluripotent stem cells are created by exogenously overexpressing the pluripotency markers (OCT4, SOX2, c-MYC, NANOG and KLF4) using a viral or non-viral vector, thereby inducing pluripotency to the transfected cell line.

Pluripotent stem cells are considered to be undifferentiated when they have not committed to a specific lineage. ESCs are considered to be undifferentiated when they have not committed to a specific differentiation lineage. Such cells display morphological characteristics that distinguish them from differentiated cells of embryo or adult origin. Undifferentiated ESCs are easily recognized by those skilled in the art, and typically appear in the two dimensions of a microscopic view in colonies of cells with high nuclear/cytoplasmic ratios and prominent nucleoli. Undifferentiated ESCs express genes that may be used as markers to detect the presence of undifferentiated cells, and whose polypeptide products may be used as markers for negative selection.

The term "treating" or "treatment" refers to reducing, ameliorating reversing, alleviating, inhibiting the progress of, or preventing a disease or a medical condition such as cancer. In another aspect, the term also encompasses prophylaxis, therapy and cure. The subject or patient receiving "treatment," or whom undergoes "treating" is any mammal in need of such treatment for cancer, including primates, and humans, and other mammals such as equines, cattle, swine and sheep; and domesticated mammals and pets.

Reprogramming: Reprogramming cells using MIP, or any vector that generates similar cancer vaccine properties as to be expected to be the result of the MIP plasmid.

Somatic cells of interest include, but are not limited to, fibroblasts, blood cells, urine cells, etc.

Adjuvant: An adjuvant is an immunological agent that boosts the immunological response of the recipients' immune system to target the pluripotent stem cells. The adjuvant includes those disclosed in the present application and those known in the art for boosting the immunological response of the recipients' immune system to target the pluripotent stem cells. The term "adjuvant" refers to any substance or agent that can stimulate an immune response. Some adjuvants can cause activation of a cell of the immune system. For example, an adjuvant can cause an immune cell to produce and secrete a cytokine. Examples of adjuvants that can cause activation of a cell of the immune system include, but are not limited to, the nanoemulsion formulations described herein, saponins purified from the bark of the $Q.\ saponaria$ tree, such as QS21, poly(di(carboxylatophenoxy)phosphazene (PCPP polymer; Virus Research Institute, USA); derivatives of lipopolysaccharides such as monophosphoryl lipid A (MPL; RibiImmunoChem Research, Inc., Hamilton, Mont.), muramyl dipeptide (MDP; Ribi) and threonyl-muramyl dipeptide (t-MDP; Ribi); OM-174 (a glucosamine disaccharide related to lipid A; OM Pharma SA, Meyrin, Switzerland); cholera toxin (CT), and Leishmania elongation factor (a purified Leishmania protein; Corixa Corporation, Seattle, Wash.); or a mixture thereof. Other adjuvants known in the art may include, for example, aluminum phosphate or hydroxide salts. In some embodiments, for example, the pluripotent stem cells of the present invention are administered with one or more adjuvants. In some embodiments, the adjuvants employed are described in US2005158329; US2009010964; US2004047882; or U.S. Pat. No. 6,262,029.

As used herein, the clause "an amount effective to boost (or induce) an immune response" (for example, a composition for inducing or boosting an immune response), refers to the dosage level or amount required (for example, when administered to a mammal) to stimulate, generate and/or elicit an immune response in the mammal. An effective amount can be administered in one or more administrations over different time periods, as disclosed herein (for example, via the same or different route). The application or dosage is not intended to be limited to a particular formulation or an administration route or time period.

A tumor-associated antigen (TAA) or tumor-specific antigen (TSA), as used herein, refers to known and also unknown antigens/epitopes present on cancer cells.

An optimal immune response with the cancer vaccine is to prime the host's immune system to target these TAAs and TSAs, present on pluripotent cells, and provide immunity to cancer types that express the TAAs and TSAs.

Known TAAs and TSAs include, but are not limited to, EPCAM, CEACAM, TERT, WNK2, survivin, etc. (all Onco; Bushman Lab, University of Pennsylvania).

Methods of Vaccination:

Pluripotent stem cells as a source for the cancer vaccine may be obtained from any mammalian species, including, for example, human, primate, equine, bovine, porcine, etc. but particularly human cells.

Pluripotent stem cells are grown using standard methods known in the art, such as in feeder cell free conditions until a stable pluripotent stem cell population is formed. This population should include a >90% pure pluripotent stem cell percentage as assessed by pluripotent stem cell sorting using magnetic antibody sorting (MACS) or fluorescent antibody sorting (FACS).

The cell dose (range from $1 \times 10^6$ to $1 \times 10^9$) used for the cancer vaccine may need to be adjusted to the mammal that the vaccine is used for. In small rodents, effectiveness of the vaccine was set at $2 \times 10^6$ pluripotent stem cells per dose.

Pluripotent stem cells are to be irradiated prior to vaccination to prevent teratoma formation at the injection site. This dose should be adjusted according to pluripotent stem cell sensitivity or resistance to arresting cell cycle. For iPSCs generated from small rodents, e.g. mice, this dose was set to 6000 rads (range from 1000-10000 rads).

The site of vaccination should be in the subcutaneous space to allow for proper antigen presentation to the immune system. The location of where the vaccine should be placed may change based on the subjects' morphology, but should be performed at different injection sites to avoid local immune suppressive responses. In one embodiment, the method may be performed for a total of four weekly rounds of vaccination over the course of four weeks. In another embodiment, the method may be performed daily, several times a week, or every two weeks, and the duration could be two, three, four, five, six, seven, or 8 weeks. The number of vaccinations depends on the subject's immune response towards the vaccine and priming conditions, and therefore, may be adjusted accordingly during treatment.

In another embodiment, the pluripotent cells in this invention can also be genetically altered to enhance their immunogenic properties or make them more suitable in priming the host's immune response to targeting TSAs and TAAs.

Small molecular agents or biologic compounds can be used in conjunction with the C+I vaccine to increase the cytotoxic potential of the C+I primed immune cells towards cancer cells. Such molecular agents or biologic compounds may include, for example, diprovocim, a PD-1 or PDL-1 inhibitor, etc.

In one embodiment, the therapeutic dose of the adjuvant will depend on the adjuvant being used for the cancer vaccine. In the original description of the cancer vaccine using the adjuvant CpG, the dose was set at a working concentration of 5 µM. However, depending on the mammal and type of cancer being treated, a factor of 10 dilution or concentration of the adjuvant may be used, such as a concentration of 0.05 µM, 0.03 µM, 0.01 µM; or 10 µM, 30 µM, or about 50 µM. It will be understood by one of skill in the art that such guidelines will be adjusted for the molecular weight of the active agent, and also based on the effectiveness of the adjuvant for the specific treatment. The dosage may also be varied for type of mammal receiving the vaccine.

Experimental

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.), but some experimental errors and deviations should be accounted for. Unless indicated otherwise, parts are parts by weight, molecular weight is weight average molecular weight, temperature is in degrees Centigrade (° C.), and pressure is at or near atmospheric.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

For further elaboration of general techniques useful in the practice of this invention, the practitioner can refer to standard textbooks and reviews in cell biology, tissue culture and embryology. With respect to tissue culture and ESCs, the reader may wish to refer to Teratocarcinomas and embryonic stem cells: A practical approach (E. J. Robertson, ed., IRL Press Ltd. 1987); Guide to Techniques in Mouse Development (P. M. Wasserman et al. eds., Academic Press 1993); Embryonic Stem Cell Differentiation in Vitro (M. V. Wiles, Meth. Enzymol. 225:900, 1993); Properties and uses of Embryonic Stem Cells: Prospects for Application to Human Biology and Gene Therapy (P. D. Rathjen et al., Reprod. Fertil. Dev. 10:31, 1998).

General methods in molecular and cellular biochemistry can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle &

Griffiths, John Wiley & Sons 1998). Reagents, cloning vectors, and kits for genetic manipulation referred to in this disclosure are available from commercial vendors such as BioRad, Stratagene, Invitrogen, Sigma-Aldrich and ClonTech.

Example 1 iPSC-Based Cancer Vaccination: An Autologous Stem Cell Vaccine Against Cancer

We demonstrate that we can harness the immunogenic and tumorigenic properties of autologously-derived iPSCs into a cancer vaccine. Using multiple mouse strains and multiple cancer types, we show in vitro and in vivo efficacy of using iPSCs to prime the hosts' immune system in targeting cancer, either completely inhibiting tumor establishment or significantly reducing tumor growth. Accordingly, the present vaccination method provides complete inhibition of tumor establishment or significantly reduced the tumor growth.

Furthermore, we provide in-depth analysis of the immune cells responsible for the immune response at different stages. We also demonstrate efficacy of the vaccine as an adjuvant immunotherapy after tumor resection, resulting in reactivation of the immune system in targeting the cancer and clearing it from the resection areas.

Tumor establishment and progression consists of highly proliferative hypoimmunogenic cells that evade the surveillance of the immune system. Therefore, new avenues within the field of cancer treatment are being pursued towards reactivating the immune system in targeting cancer. One way researchers are trying to achieve this is by using chimeric antigen receptors (CARs) with promising results. The idea behind this therapy is to create a cancer-specific antigen receptor and couple this to an effector cell, e.g. T-cell, with newer generations of CARs even incorporating the co-stimulatory pathways. However, outcomes have been variable with patients relapsing, possibly due to loss of expression of the targeted antigen. A way to circumvent this would be to identify new tumor-specific antigens, although large numbers of tumor antigens are still unknown.

Pluripotent stem cells (PSCs) and cancer tissues share known, but likely also unknown, TSAs and TAAs with cancer cells and therefore could be a potential agent to prime an immune system to target cancer. This cell would then function as a surrogate cell type that resembles the targeted cancer type. The usage of embryonic cells for priming of the immune system in targeting cancer has failed in showing efficacy and safety for the treatment of various types of cancer and have relied on the use the ethically burdened ESCs and a genetically modified cell line, overexpressing GM-CSF, as an adjuvant (Yaddanapudi et al., 2012). These last components making these treatments unsuitable for clinical translation.

Using FVB strain iPSCs (Figure S2A, D) and the adjuvant CpG proven to be successful in tumor vaccination (Gilkeson et al., 1998; Goldstein et al., 2011; Mor et al., 1997; Mukherjee et al., 2007), we observed an effective immune response to a murine breast cancer (DB7) with a CpG-iPSC (C+I) combination. In brief, we first established the effect of CpG and an optimal vaccination schedule. We primed FVB mice with iPSCs or C+I for two weeks or four weeks and found the strongest in vitro T-cell responses to DB7 tumor lysate in the C+I four-week group (Figure S2E, F). In addition, a vaccination schedule of four weeks with the C+I combination resulted in the highest IgG binding (80.0±3.4%) to DB7 and was therefore used for subsequent vaccination rounds (FIG. 1A, B).

After optimizing the vaccination schedule, we proceeded with the vaccination of 40 FVB mice, divided into four groups: 1) PBS, 2) CpG only, 3) iPSC only, and 4) C+I. After 4 once-weekly vaccinations, $5 \times 10^4$ DB7 cancer cells were injected subcutaneously and tumor size was monitored using caliper measurement. After one week, all mice presented with a similar lesion at the injection site that regressed in 7 out of 10 C+I treated mice and progressed to larger tumors in the other groups (FIG. 2A, B; Figure S3A, B). Four weeks after tumor inoculation, five mice per group were sacrificed to analyze the immune profiles in blood, spleen, and draining lymph nodes (dLNs). The other five mice per group were used for long-term survival studies for up to one year. Most were sacrificed in the first two weeks after the end of the experiment due to tumor sizes larger than 1 cm$^3$. However, two mice in the C+I treatment group survived one year and had antibody titers against iPSCs and DB7 similar to the start of the experiment and were able to fully reject $5 \times 10^4$ cancer cells upon reintroduction (Figure S3C, D). The control mice in this experiment, primed with iPSC-derived endothelial cells, were unable to mount IgG responses to the DB7 cell line, thereby ruling out the possibility that the culturing conditions with FBS-containing media could be responsible for the cross-reactivity or endogenous murine leukemia viral antigens.

To demonstrate the effectiveness of our vaccine in targeting multiple cancer types, an experiment was performed using the melanoma cell line B16F0, syngeneic to the C57BL/6 mouse strain. C57BL/6 iPSCs were generated (Figure S2B, D) and 40 mice were again divided into PBS, CpG, iPSC, and C+I groups and treated weekly for four weeks. Following this, $5 \times 10^4$ B16F0 cells were subcutaneously injected in the lower back. Tumor growth assessment by caliper measurement showed significantly lower tumor progression by week 2 in the C+I group (FIG. 2C, D; Figure S3E, F). Due to large tumor sizes in the control groups, the mice were sacrificed two weeks after tumor injection. Afterwards, the immune cell profiles in blood, dLNs, and spleens were analyzed using flow cytometry. Cytometric analysis in the C+I group showed a significant decrease in regulatory T-cells (T-regs) in blood and an increase in effector/memory helper T-cells in the dLNs at two weeks post tumor injections in C57BL/6 mice (FIG. 3A, B), as well as increased percentages of mature antigen presenting cells (APCs) (FIG. 3C).

At a later stage of tumor rejection (4 weeks), FVB mice in the C+I vaccinated group had significant increases in the effector/memory cytotoxic T-cells in the spleen in addition to their increased frequency in the dLNs (FIG. 3D, F). The tumor-specificity of these cytotoxic T-cells was further confirmed by increased secretion of IFN-γ by splenocytes isolated from C+I vaccinated mice in response to DB7 tumor lysate (FIG. 4A, B, Figure S4A, B). As with the C57BL/6 mice, upregulation of mature APCs and helper T-cells was also seen in the dLNs of FVB mice (Figure S4C-F).

Both the C57BL/6 and the FVB mouse strains remained healthy throughout the study and showed no signs of autoimmune responses due to the vaccine (Figure S7).

The effectiveness of the C+I vaccine was assessed in the more clinically relevant orthotopic model of breast cancer. Significant tumor size differences were seen as early as one week after orthotopic transfer of cancer cells in C+I vaccinated mice compared to vehicle control, followed by further tumor reduction over the course of three weeks (FIG. 4C, E). Using an additional group of orthotopic breast cancer mice, in vivo tumor specificity was tested by adoptively transferring splenocytes from C+I vaccinated or vehicle vaccinated mice into these tumor-bearing mice (FIG. 4D). This resulted in a significant reduction of tumor sizes in the C+I vaccinated group compared to the vehicle vaccinated group (FIG. 4F).

As a model for prophylactic treatment, we selected the mesothelioma cell line AC29, syngeneic to CBA/J mice. CBA/J iPSCs were created (Figure S2C, D) and mice were vaccinated weekly for four weeks with PBS (P), CpG and iPSCs (C+I), or CpG with irradiated AC29 cancer cells (C+A) as a positive control. Afterwards, $2\times10^6$ AC29 cells (A) or $2\times10^6$ iPSCs (I) were injected subcutaneously, and after one week the TILs were analyzed for their immune profile and TCR sequences. Immune profiling was performed with cytometry by time of flight (CyTOF) analysis using a phenotype and intracellular staining kit, which revealed increased presence of effector/memory $CD4^+$ (24.0%) and $CD8^+$ T-cells (22.4%), with a reduction in T-regs in the C+I/A group (1.9%) compared to P/A control (21.1%, 14.2% and 3.0%, respectively) (FIG. 5A). Using Citrus (cluster identification, characterization and regression) analysis, B-cells and T-cells expressing IL-2, IL-4, and IL-5 were found to be predictive for tumor regression in C+I vaccinated mice compared to the PBS control group (FIG. 5B; Figure S5A-B, D). Systemic cytokine levels were significantly lower in the vaccinated group and were found to correlate with the positive control mice of tumor rejection (C+I/iPSC; C+A/AC29) (FIG. 6A; Figure S6A-B).

TCR sequencing in the PBS control group revealed overlap in T-cell clones that are commonly present in thymus and spleen (Figure S6C). In contrast, the TCRs in the C+I group were more diverse between different mice. Also, there was a generally lower frequency of the clones in the thymus and more similar frequencies in the spleen, likely on the basis of mouse-specific responses to the C+I vaccine (FIG. 6B; Figure S6D). There was one TCR clone that was shared by 4 out of 5 mice in the C+I group, was not present in any of the other groups, and was also extremely rare in naïve mice.

To assess effectiveness of the vaccine as an adjuvant therapy after tumor resection, we next injected $5\times10^4$ B16F0 tumor cells subcutaneously in the lower back of C57BL/6 mice and R2 or R1 resected the tumors after two weeks. R2 resected mice had no visible recurrence of melanoma in the resection area (RA) after receiving two adjuvant rounds of C+I vaccine, whereas PBS control vaccinated mice had visible tumors within the RAs (Figure S7A).

In R1 resected mice that were vaccinated for four weeks with the C+I vaccine (n=10), CpG (n=10), and PBS (n=8) (FIG. 7A), dLNs and the RAs were analyzed using a tumor-specific primer designed to detect and quantify the B16F0 melanoma line (Figure S7B-G). Tumor load in the dLNs was reduced in both the CpG only and the C+I vaccine group, indicating the effect of CpG as a potent adjuvant that induces tumor degradation upon near-tumor injection (Figure S7H). More distant from the vaccination sites, only the C+I vaccinated group had significantly lower tumor recurrence in the RA (FIG. 7B). Systemically, this is explained by reactivation of the immune system, as well as a reduction of B16 melanoma-promoting Th17 cells compared to the control groups (FIG. 7C; Figure S5C, E).

Methods Summary:

Animal models. For the various experiments (see sections "CpG+iPSC vaccine preparation and immunization" and "Cancer cell lines and implantation"), young adult female FVB, C57BL/6J and CBA/J mice (6-8 weeks-old) were used. Animals were randomly assigned to the different treatment groups. Tumor-bearing mice were excluded from the experiment if their physical condition required euthanasia before the experimental deadline, which included tumor sizes larger than 1 $cm^3$, visible distress, pain, or illness. All experiments were approved by the Stanford University Administrative Panel of Laboratory Animal Care (APLAC).

Generation of murine iPSCs from fibroblasts. Fibroblasts from FVB, C57BL/6J, and CBA/J mice (The Jackson Laboratory, Bar Harbor, Me.) were grown in DMEM Glutamax (ThermoFisher Scientific, Waltham, Mass., USA) with 20% fetal bovine serum (FBS) and 1× NEAA (ThermoFisher Scientific). Fibroblasts were dissociated using TrypLE Express (ThermoFisher Scientific) and $1\times10^6$ fibroblasts were resuspended in electroporation buffer (Neon system, ThermoFisher Scientific). Cells were transfected with a novel codon optimized mini-intronic plasmid (coMIP) containing the four reprogramming factors Oct4, Sox2, c-Myc, and KLF4 (Diecke S, Lu J, Lee J, Termglinchan V, Kooreman N G, Burridge P W, Ebert A D, Churko J M, Sharma A, Kay M A, Wu J C. Sci Rep. 2015 Jan. 28; 5:8081. doi: 10.1038/srep08081. PMID: 25628230). After transfection, cells were plated on irradiated mouse embryonic feeder (MEF) cells and cultured in DMEM with 15% FBS, 1×NEAA, and 10 ng/ml murine leukemia inhibiting factor (mLIF; EMD Millipore, Mass., USA). After iPSC colonies started to appear, these were manually picked and transferred to a fresh feeder layer. The iPSC colonies were grown out and after a few passages transferred to 0.2% gelatin-coated plates and sorted for SSEA-1 using magnetic bead sorting (Miltenyi, Germany) to keep a pure undifferentiated population. For characterization, iPSCs were stained for Oct4, Nanog, Sox2 (Santa Cruz, Calif., USA), SSEA1, and c-Myc (EMD Millipore) to assess pluripotency. In addition, a teratoma assay was performed on all iPSC lines by transplantation of $1\times10^6$ iPSCs in the hindlimb of NOD-SCID mice (The Jackson Laboratory). All cell lines were tested for *mycoplasma* contamination and found to be negative.

CpG+iPSC vaccine preparation and immunization. Per mouse, $2\times10^6$ SSEA-1-sorted syngeneic murine iPSCs were irradiated at 6,000 rads prior to injection. Cells were suspended in 100 µl of 5 µM CpG (Invivogen, San Diego, USA), dissolved in PBS, and loaded into ¼ cc insulin syringes (Terumo). Mice were placed in an induction chamber and anesthetized with 2% isoflurane (Isothesia, Butler Schein) in 100% oxygen with a delivery rate of 2 l/min until loss of righting reflex, as per guidelines of the APLAC at Stanford University. Immunization was performed by subcutaneous injection of the vaccine in the flank of the mice, changing the injection site every week. Mice were monitored weekly for early signs of auto-reactivity to the vaccine by weight measurements and gross examination of overall appearance. Vaccination preparation and dosage were the same for the prophylactic and adjuvant treatment experiments.

Cancer cell lines and implantation. The breast cancer line DB7 was a gift from Dr. Joe Smith (University of Utah, USA). It was derived from FVB mice and is a non-metastatic cell line. The B16F0 melanoma cell line was purchased from ATCC (Manassas, Va., USA) and is syngeneic to C57Bl/6 mice. It has low-grade lymphoid metastatic potential to the lungs. The AC29 mesothelioma cancer line was purchased from Sigma-Aldrich (St. Louis, Mo., USA). All cell lines were tested for *mycoplasma* contamination and found to be negative. The cancer lines were grown in DMEM, 10% FBS under normal culture conditions. For the C57BL/6 and FVB mice, $5\times10^4$ cancer cells were resuspended in 100 µl PBS and injected subcutaneously in the lower back of the mice. The CBA/J mice were injected with $2\times10^6$ cancer cells. Tumor growth was assessed weekly by caliper measurement. At the end of the study, tumors were explanted and gross examination of draining lymph nodes and lung tissue was performed for any metastases.

IgG binding assay. Cells were washed multiple times with PBS and resuspended in 100 µl FACS buffer with the addition of 2 µl of serum from the vaccinated mice and incubated for 30 minutes at 4° C. Following this, cells were washed multiple times and incubated with an anti-IgG FITC secondary antibody (ThermoFisher Scientific) for another 20 min at 4° C. As an isotype control, an IgG antibody, pre-adsorbed for murine IgG and IgM, was included. The cells were then analyzed using the LSR-II Flow Cytometer.

Cytometry by Time of Flight (CyTOF). Immune cells were isolated from explanted tissues according to the above-mentioned methods. Cells were stained with the Mouse Spleen/Lymph Node Phenotyping kit, the Mouse Intracellular Cytokine I Panel kit and the viability dye Cisplatin (Fluidigm, South San Francisco, Calif., USA). Cells were resuspended in MaxPar water at a concentration of $1\times10^5$-$1\times10^8$ cells per ml with the addition of normalization beads and ran on a CyTOF2 (Fluidigm) machine. The data was normalized using the normalization beads. The data was analyzed using the Cytobank online software for spanning-tree progression analysis of density-normalized events (SPADE) (Mountain View, Calif., USA).

Cluster identification, characterization and regression (Citrus). In brief, based on hierarchical clustering and a regularized regression model, Citrus generates a list of stratifying clusters and behaviors from multidimensional data. In addition, it can describe the features (e.g., intracellular cytokines) of these clusters and provide a predictive model for newly acquired data or validation samples. The stratifying features from these clusters are plotted as median expression on the x-axis (FIGS. 5B, 7C; Figure S5B). CyTOF data was analyzed using Cytobank and gated for viable single cells, following which the FCS files were uploaded in the GUI from Citrus 0.8 and the script was run in R (version 3.0.3). For the analysis of the splenocytes exposed to B16F0 tumor lysate, Citrus analysis was performed with 10,000 sampling events with 0.2% (567 events) minimum clustering. For the TILs, Citrus analysis was based on 1,000 sampling events with 500 events minimum clustering. Clustering features were found to be of interest with a cv.min and cv.fdr. constrained of less than 25.

PCR detection of the large genomic deletion in CDKN2A. Primers were designed to detect the junction of the large deletion in CDKN2A of the B16 melanoma cell line (Figure S1E). Each 25 µl PCR reaction solution contained 1.25 units of PrimeSTAR® GXL DNA Polymerase (Clontech) and 50-100 ng of genomic DNA extracted by DNeasy Blood & Tissue Kit (Qiagen) (Figure S7C). PCR products were then analyzed by Sanger sequencing and aligned with the gene database in NCBI (Figure S7D).

Quantification of tumor load for melanoma by digital droplet PCR (ddPCR). Primers and probe were designed to detect 3 SNPs (colored in red) that are specific to the B16 melanoma cell line. DNA was extracted from the tumor resection area and dLNs of C57BL/6 mice four weeks after R1 tumor resection using the DNeasy Blood & Tissue Kit (Qiagen). Each ddPCR reaction solution was reconstituted to a final volume of 20 µl using 40 to 50 ng of DNA template and ddPCR™ Supermix for Probes, without dUTP (Bio-Rad). Each sample was quantified by using 2 probes: MT probe to assess the tumor load, and TaqMan® Copy Number TFRC probe (Mm00000692_cn, ThermoFisher) to assess the cell amount (Figure S7E, F). The final primer and probe concentrations were 900 nM and 250 nM, respectively. Droplet formation was carried out using a QX100 droplet generator with 20 µL of PCR reaction solution. A rubber gasket was placed over the cartridge and loaded into the droplet generator. The emulsion (~35 µl in volume) was then slowly transferred using a multichannel pipette to a 96-Well Twin.Tec™ PCR Plates (Eppendorf). The plate was then heat-sealed with foil and the emulsion was cycled to end point per the manufacturer's protocol with annealing temperature at 62.5° C. The samples were then read using a BioRad QX100 reader. The standard curve was created for different amounts of tumor load, including 0%, 1%, 5%, 10%, 25%, 50%, 75%, 90%, 95%, 99%, and 100%, and linear regression equation was utilized to quantify the tumor load for each DNA sample (Figure S7G). Following are the sequences of the primers and probes for detecting tumor load:

Forward primer, 5'ACTAGCCAGAGGATCTTAAA-GACT3';
Reverse primer, 5'GCCATCACTGGAAAGAGAGGC3';
Mutant Probe, 5'(HEX) CCTGCCCACC-CACTCCCCCTTTTT (Blackhole Quencher) 3'; (red indicating mutant-specific alleles).

T-cell Receptor (TCR) sequencing. The DNA from the TILs infiltrating the AC29 tumors was isolated using the DNeasy Blood & Tissue kit (Qiagen). Samples were submitted to Adaptive Biotechnologies (Seattle, Wash., USA) for a survey level TCR sequencing. The minimum DNA content from the submitted samples was 150 ng per sample with DNA quality A260/280 between 1.8 to 2.0. Data analysis as well as assessing TCR clonality between samples was done in collaboration with Adaptive Biotechnologies. A list of TCR clones within each sample and their frequencies within the DNA sample were provided. For the T-cell overlap search, the amino acid sequences of the clones appearing in 4 or 5 of the samples in the two sample groups were compared. Data from the C+I treatment group and the PBS control group were ruled comparable with similar average productive unique values (PBS: 3582.2, CI: 3005.4).

ELISPOT assay. Splenocytes ($5\times10^5$) were isolated as described before and co-cultured with either iPSC or DB7 lysate (35 µg) for the duration of 37 hours after which secretion of granzyme-β and IFN-γ was measured by Enzyme-Linked ImmunoSpot (ELISPOT) according to the manufacturer's instructions (cat #ELD5819, R&D Systems, Diaclone). Adobe Photoshop CS6 software was used for the calculation of size and number of IFN-r positive spots.

Adoptive transfer of splenocytes. C+I vaccinated (n=20) and vehicle vaccinated (n=20) mice were sacrificed and their splenocytes isolated. The spleens were digested and passed through a 70 µm strainer. Afterwards red blood cells were lysed with ACK lysis buffer (cat #118-156-101, Quality biology, Inc.) and the remaining splenocytes washed with PBS. The splenocytes were then dissolved in 200 µl PBS solution and intravenously injected in an orthotopic model of breast cancer by tail vein injection.

Orthotopic tumor model. FVB mice were injected with $2\times10^6$ DB7 tumor cells directly into the mammary fat pad tissue. The range of cancer cell number was based on previous reports and was set at $2\times10^6$ DB7 cancer cells after validating the model and achieving a tumor incidence of 100%.

Statistics. All values are expressed as mean±s.d. or mean±s.e.m. as indicated. Intergroup differences were appropriately assessed by either unpaired two-tailed Student's t-test or one-way/two-way analysis of variance (ANOVA) with Tukey's multiple comparison tests using GraphPad software. *P<0.05, P<0.01, *P<0.001, ****P<0.0001.

The entire disclosure of all documents, including patents and publications cited throughout this application are incorporated herein by reference in their entirety as if each individual publication or patent application were specifically and individually indicated to be incorporated by reference.

What is claimed is:

1. A method for the treatment of cancer in a patient, the method comprises a vaccination of the patient with a vaccine, wherein the vaccine comprises an effective amount of mammalian pluripotent stem cells obtained by reprogramming of somatic cells from the patient and the vaccine further comprises an adjuvant that is an immunological agent to boost the immune response towards the vaccine and, wherein the vaccination comprising the step of administering mammalian pluripotent stem cells to the patient in need thereof.

2. The method of claim 1 wherein the pluripotent stem cells are induced pluripotent stem cells (iPSCs).

3. The method of claim 1, wherein the mammalian pluripotent stem cells are undifferentiated pluripotent stem cells.

4. The method of claim 1, wherein the pluripotent stem cells are generated using a mini-intronic plasmid containing four reprogramming factors comprising Oct4, c-Myc, KLF-4 and Sox2, with the possible addition of shRNA p53.

5. The method of claim 1, wherein the stem cells are obtained by reprogramming somatic cells selected from the group consisting of fibroblast, keratinocytes, peripheral blood cells and renal epithelial cells.

6. The method of claim 1, wherein the vaccine is administered according to at least one of the following methods: a) as a standalone vaccination; b) as an adjuvant therapy before tumor resection; c) as an adjuvant therapy after tumor resection, d) in a metastatic setting; e) as a preventative setting in the absence of tumor or cancer; and f) in combination with chemotherapy, immunotherapy, targeted therapies, using biologic agents, using small molecule agents, with nanoparticles comprising the biologic or small molecule agents, or a combination thereof.

7. The method of claim 1, wherein the cancer is selected from the group consisting of breast cancer, melanoma and mesothelioma.

8. The method of claim 1, wherein the cancer is selected from the group consisting of leukemia, multiple myeloma, Hodgkin's lymphoma, non-Hodgkin's lymphoma, lymphoma, myeloproliferative disorders, squamous cell cancer, adenocarcinoma, sarcoma, neuroendocrine carcinoma, bladder cancer, skin cancer, brain and spinal cord cancers, head and neck cancer, thyroid, bone cancer, breast cancer, cervical cancer, colorectal cancer, endometrial cancer, gastrointestinal cancers, (hypo) laryngeal cancer, esophageal cancer, liver cancer, lung cancer, pancreatic cancer, prostate cancer, eye cancer, renal cell cancer, kidney, hepatic, ovarian cancer, gastric cancer, testicular cancer, thyroid and thymus cancer.

9. A method for the vaccination of a mammal with a pluripotent stem cell cancer vaccine, the method comprising:
   introducing the mammalian pluripotent stem cells obtained by reprogramming from a somatic cell from the recipient, wherein the vaccine further comprises an adjuvant where the adjuvant is an immunological agent to boost the immune response towards the vaccine; and providing the recipient with the vaccine.

10. The method of claim 9, wherein the mammalian cells are undifferentiated pluripotent cells.

11. The method of claim 10, wherein the pluripotent stem cells are generated using a mini-intronic plasmid containing four reprogramming factors comprising Oct4, c-Myc, KLF-4 and Sox2.

12. The method of claim 9, wherein the pluripotent stem cells are obtained by reprogramming somatic cells selected from the group consisting of fibroblast, keratinocytes, peripheral blood cells and renal epithelial cells.

13. The method of claim 9, wherein the vaccine is irradiated prior to vaccination.

14. A thermally stable vaccine composition comprising an effective amount of mammalian pluripotent stem cells obtained by reprogramming of somatic cells from a mammal, and an adjuvant or an immunological agent to boost the immune response towards the vaccine.

15. The vaccine composition of claim 14, wherein the pluripotent stem cells are induced pluripotent stem cells (iPSCs).

16. The vaccine composition of claim 14, wherein the mammalian pluripotent stem cells are undifferentiated pluripotent stem cells.

17. The vaccine composition of claim 14, wherein the stem cells are obtained by reprogramming somatic cells selected from the group consisting of fibroblast, keratinocytes, peripheral blood cells and renal epithelial cells.

18. The vaccine composition of claim 14, wherein the adjuvant is selected from the group consisting of CpG, QS21, poly(di(carboxylatophenoxy)phosphazene; derivatives of lipopolysaccharides such as monophosphoryl lipid A, muramyl dipeptide (MDP; Ribi), threonyl-muramyl dipeptide (t-MDP; Ribi); OM-174; cholera toxin (CT), and Leishmania elongation factor.

* * * * *